(12) United States Patent
Rava et al.

(10) Patent No.: US 6,690,966 B1
(45) Date of Patent: *Feb. 10, 2004

(54) METHODS OF MOLECULAR SPECTROSCOPY TO PROVIDE FOR THE DIAGNOSIS OF TISSUE

(75) Inventors: Richard P. Rava, Palo Alto, CA (US); Joseph J. Baraga, Somerville, MA (US); Michael S. Feld, Waban, MA (US)

(73) Assignee: Massachusetts Institute of Technology, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/107,854

(22) PCT Filed: Jan. 17, 1992

(86) PCT No.: PCT/US92/00420

§ 371 (c)(1),
(2), (4) Date: Oct. 22, 1993

(87) PCT Pub. No.: WO92/15008

PCT Pub. Date: Sep. 3, 1992

Related U.S. Application Data

(63) Continuation-in-part of application No. 07/661,077, filed on Feb. 26, 1991, now abandoned.

(51) Int. Cl.[7] .................................................. A61B 5/00

(52) U.S. Cl. ....................... 600/473; 600/475; 600/477; 600/478

(58) Field of Search ................................ 128/633, 634, 128/664; 356/301; 600/310, 311, 473, 475, 476–479

(56) References Cited

U.S. PATENT DOCUMENTS

| 3,327,117 A | 6/1967 | Kamentsky | ................ | 250/83.3 |
| 3,327,119 A | 6/1967 | Kamentsky | ................ | 250/83.3 |
| 3,461,856 A | 8/1969 | Polanyi | ................. | 128/2 |

(List continued on next page.)

FOREIGN PATENT DOCUMENTS

| RU | 922-050 | 4/1978 |
| WO | 84/04665 | 12/1984 |
| WO | 89/02718 | 4/1989 |

OTHER PUBLICATIONS

Nie et al., "Applications of Near–Infrared Fourier Transform Raman Spectroscopy in Biology and Medicine" *Spectroscopy*, 5(7):pp 24–32.

Alfano et al., "Human Breast Tissues Studies by IR Fourier Transform Raman Spectroscopy" *Laser In The Life Sciences*, 4(1):23–28, (1991).

Halaby et al., "Computer–Controlled Spectral Measurements of Blood Cells" *Transactions on Biomedical Engineering*, BME–26(1): (Jan. 1979).

Parker et al., "Infrared Studies of Human and Other Tissues by the Attenuated Total Reflection Technique [1,2]" *Analytical Biochemistry*, 18, 414–422 (1967).

(List continued on next page.)

*Primary Examiner*—Ruth S. Smith
(74) *Attorney, Agent, or Firm*—Bowditch Dewey, LLP

(57) ABSTRACT

Systems and methods for spectroscopic diagnosis and treatment are employed which utilize molecular spectroscopy to accurately diagnose the condition of tissue. Infrared Raman spectroscopy and infrared attenuated total reflectance measurements are performed utilizing a laser radiation source and a fourier transform spectrometer. Information acquired and analyzed in accordance with the invention provides accurate details of biochemical composition and pathologic condition.

16 Claims, 20 Drawing Sheets

U.S. PATENT DOCUMENTS

| | | | |
|---|---|---|---|
| 3,647,299 A | | 3/1972 | Lavallee ..................... 356/41 |
| 4,213,462 A | | 7/1980 | Sato ........................... 128/634 |
| 4,290,433 A | | 9/1981 | Alfano ....................... 128/665 |
| 4,427,889 A | * | 1/1984 | Muller ....................... 128/633 |
| 4,449,535 A | | 5/1984 | Renault ...................... 128/634 |
| 4,479,499 A | | 10/1984 | Alfano ....................... 128/665 |
| 4,515,165 A | | 5/1985 | Carroll ....................... 128/664 |
| 4,556,057 A | | 12/1985 | Hiruma et al. ............ 128/303.1 |
| 4,620,284 A | * | 10/1986 | Schnell et al. .............. 356/301 |
| 4,641,650 A | | 2/1987 | Mok ........................ 128/303.1 |
| 4,718,417 A | | 1/1988 | Kittrell et al. ............ 128/303.1 |
| 4,737,628 A | | 4/1988 | Lovoi ......................... 128/395 |
| 4,758,081 A | | 7/1988 | Barnes ........................ 351/221 |
| 4,768,516 A | | 9/1988 | Stoddart et al. ............ 128/665 |
| 4,894,547 A | | 1/1990 | Leffell et al. ............. 250/461.2 |
| 4,930,516 A | | 6/1990 | Alfano et al. ............... 128/665 |
| 4,981,138 A | | 1/1991 | Deckelbaum et al. ....... 128/665 |
| 5,115,137 A | * | 5/1992 | Andersson-Engels et al. .......................... 128/633 |
| 5,261,410 A | * | 11/1993 | Alfano et al. ............... 128/664 |
| 5,293,872 A | * | 3/1994 | Alfano et al. ............... 128/664 |

OTHER PUBLICATIONS

Williamson et al., "Near–Infrared Raman Spectroscopy with a 783–nm Diode Laser and CCD Array Detector" *Applied Spectroscopy*, 43(3):372–375 (1989).

Ozaki, "Medical Application of Raman Spectroscopy" *Applied Spectroscopy Reviews*, 24(3&4):259–312 (1988).

Lewis et al., "Development of Near–Infrared Fourier Transform Raman Spectroscopy for the Study of Biologically Active Macromolecules" *Applied Spectroscopy*, 42(7):1188–1193 (1988).

Schwab et al., "Versatile, Efficient Raman Sampling with Fiber Optics", *Analytical Chemistry* 56(12):2199–2204 (1984).

Ono et al., "Fiber Optic Reflectance Spectrophotometry System For In Vivo Tissue Diagnosis" *Applied Optics* 30(1):98–105 (1991).

* cited by examiner

METHODS OF MOLECULAR SPECTROSCOPY TO PROVIDE FOR THE DIAGNOSIS OF TISSUE

RELATED TO U.S. APPLICATION

This application is a continuation-in-part of "Systems and Methods of Molecular Spectroscopy to Provide for the Diagnosis of Tissue", U.S. Ser. No. 07/661,077 filed on Feb. 26, 1991, now abandoned, by Richard P. Rava, Joseph J. Baraga, and Michael S. Feld, and is incorporated herein by reference. This application is also related to "Devices and Methods For Optical Diagnosis of Tissue" filed on Feb. 26, 1991 by G. Sargent Janes and Gary B. Hayes which corresponds to U.S. Ser. No. 07/661,072, U.S. Pat. Ser. No. 5,280,788, and is incorporated herein by reference.

GOVERNMENT SUPPORT

Funding for research conducted in connection with the subject matter of the present application was provided under NIH Grant No. RR 02594.

BACKGROUND OF THE INVENTION

In the United States heart attacks, almost entirely attributable to coronary atherosclerosis, account for 20–25% of all deaths. Several medical and surgical therapies are available for treatment of atherosclerosis; however, at present no in situ methods exist to provide information in advance as to which lesions will progress despite a particular medical therapy.

Objective clinical assessments of atherosclerotic vessels are at present furnished almost exclusively by angiography, which provides anatomical information regarding plaque size and shape as well the degree of vessel stenosis. The decision of whether an interventional procedure is necessary and the choice of appropriate treatment modality is usually based on this information. However, the histological and biochemical composition of atherosclerotic plaques vary considerably, depending on the stage of the plaque and perhaps also reflecting the presence of multiple etiologies. This variation may influence both the prognosis of a given lesion as well as the success of a given treatment. Such data, if available, might significantly assist in the proper clinical management of atherosclerotic plaques, as well as in the development of a basic understanding of the pathogenesis of atherosclerosis.

At present biochemical and histological data regarding plaque composition can only be obtained either after treatment, by analyzing removed material, or at autopsy. Plaque biopsy is contraindicated due to the attendant risks involved in removing sufficient arterial tissue for laboratory analysis. Recognizing this limitation, a number of researchers have investigated optical spectroscopic methods as a means of assessing plaque deposits. Such "optical biopsies" are non-destructive, as they do not require removal of tissue, and can be performed rapidly with optical fibers and arterial catheters. With these methods, the clinician can obtain, with little additional risk to the patient, information that is necessary to predict which lesions may progress and to select the best treatment for a given lesion.

Among optical methods, most attention has centered on ultraviolet and/or visible fluorescence. Fluorescence spectroscopy has been utilized to diagnose disease in a number of human tissues, including arterial wall. In arterial wall, fluorescence of the tissue has provided for the characterization of normal and atherosclerotic artery. However, the information provided is limited by the broad line width of fluorescence emission signals. Furthermore, for the most part, fluorescence based methods provide information about the electronic structure of the constituent molecules of the sample. There is a need for non-destructive real time biopsy methods which provide more complete and accurate biochemical and molecular diagnostic information. This is true for atherosclerosis as well as other diseases which affect the other organs of the body.

SUMMARY OF THE INVENTION

The present invention relates to vibrational spectroscopic methods using Fourier transform infrared (FT-IR) attenuated total reflectance (ATR) and near-infrared (IR) FT-Raman spectroscopy. These methods provide extensive molecular level information about the pathogenesis of disease. Both of these vibrational techniques are readily carried out remotely using fiber optic probes. In particular, a preferred embodiment utilizes FT-Raman spectra of human artery for distinguishing normal and atherosclerotic tissue. Near IR FT-Raman spectroscopy can provide information about the tissue state which is unavailable from fluorescence methods. In situ vibrational spectroscopic techniques allow probing of the molecular level changes taking place during disease progression. The information provided is used to guide the choice of the correct treatment modality.

These methods include the steps of irradiating the tissue to be diagnosed with radiation in the infrared range of the electromagnetic spectrum, detecting light emitted by the tissue at the same frequency, or alternatively, within a range of frequencies on one or both sides of the irradiating light, and analyzing the detected light to diagnose its condition. Both the Raman and ATR methods are based on the acquisition of information about molecular vibrations which occur in the range of wavelengths between 3 and 300 microns. Note that with respect to the use of Raman shifted light, excitation wavelengths in the ultraviolet, visible and infrared ranges can all produce diagnostically useful information. Near IR FT-Raman spectroscopy is ideally suited to the study of human tissue.

Raman spectroscopy is an important method in the study of biological samples, in general because of the ability of this method to obtain vibrational spectroscopic information from any sample state (gas, liquid or solid) and the weak interference from the water Raman signal in the "fingerprint" spectral region. The FT-spectrometer furnishes high throughput and wavelength accuracy which might be needed to obtain signals from tissue and measure small frequency shifts that are taking place. Finally, standard quartz optical fibers can be used to excite and collect signals remotely.

Near IR FT-Raman spectroscopy provides the capability to probe biological substituents many hundred microns below the tissue surface. In particular, for atherosclerotic tissue, calcified deposits below the tissue surface are easily discerned. Thus, it becomes possible to detect pathologic conditions which would not be apparent using angioscopic methods, as well as to study the detailed molecular basis of the pathology.

In contrast with electronic techniques, the bands in a vibrational spectrum are relatively narrow and easy to resolve. Vibrational bands are readily assigned to individual molecular groups.

The ATR technique offers several features especially suited to sampling of human tissue in vivo. Being a surface technique, the ATR method can non-destructively probe internal human tissue either by direct contact in a hollow organ (e.g. artery), or by insertion of a needle probe. In the mid-IR region, strong water absorption dominates the spectra of highly hydrated samples such as arterial tissue, obscuring the absorption from other tissue components (see FIG. 8). Accurate subtraction of the strong water absorption from FT-IR ATR spectra is relatively easy and very reliable with the high dynamic range, linearity, stability, and wavelength precision of available FT spectrometers. Furthermore, high quality mid-IR spectra of aqueous protein solutions can be collected with fiber optic ATR probes. Such probes are easily adaptable to existing catheters for remote, non-destructive measurements in vivo. The mid-IR ATR technique allows clinicians to gather precise histological and biochemical data from a variety of tissues during standard catheterization procedures with minimal additional risk.

The present methods relate to infrared methods of spectroscopy of various types of tissue and disease including cancerous and pre-cancerous tissue, non-malignant tumors or lesions and atherosclerotic human artery. Examples of measurements on human artery generally illustrate the utility of these spectroscopic techniques for clinical pathology. Results obtained demonstrate that high quality, reproducible FT-IR ATR spectra of human artery can be obtained with relative ease and speed. In addition, molecular level details can be reliably deduced from the spectra, and this information can be used to determine the biochemical composition of various tissues including the concentration of molecular constituents that have been precisely correlated with disease states to provide accurate diagnosis.

Another preferred embodiment of the present invention uses two or more diagnostic procedures either simultaneously or sequentially collected to provide for a more complete diagnosis. These methods can include the use of fluorescence of endogenous tissue, Raman shifted measurements and/or ATR measurements.

Yet another preferred embodiment of the present invention features a single stage spectrograph and charge-coupled device (CCD) detector to collect NIR Raman spectra of the human artery. One particular embodiment employs laser light in the 810 nm range to illuminate the tissue and thereby provide Raman spectra having frequency components in a range suitable for detection by the CCD. Other wavelengths can be employed to optimize the diagnostic information depending upon the particular type of tissue and the type and stage of disease or abnormality. Raman spectra can be collected by the CCD at two slightly different illumination frequencies and are subtracted from one another to remove broadband fluorescence light components and thereby produce a high quality Raman spectrum. The high sensitivity of the CCD detector combined with the spectra subtraction technique allow high quality Raman spectra to be produced in less than 1 second with laser illumination intensity similar to that for the FT-Raman system also described herein.

DETAILED DESCRIPTION

Figure 1A:
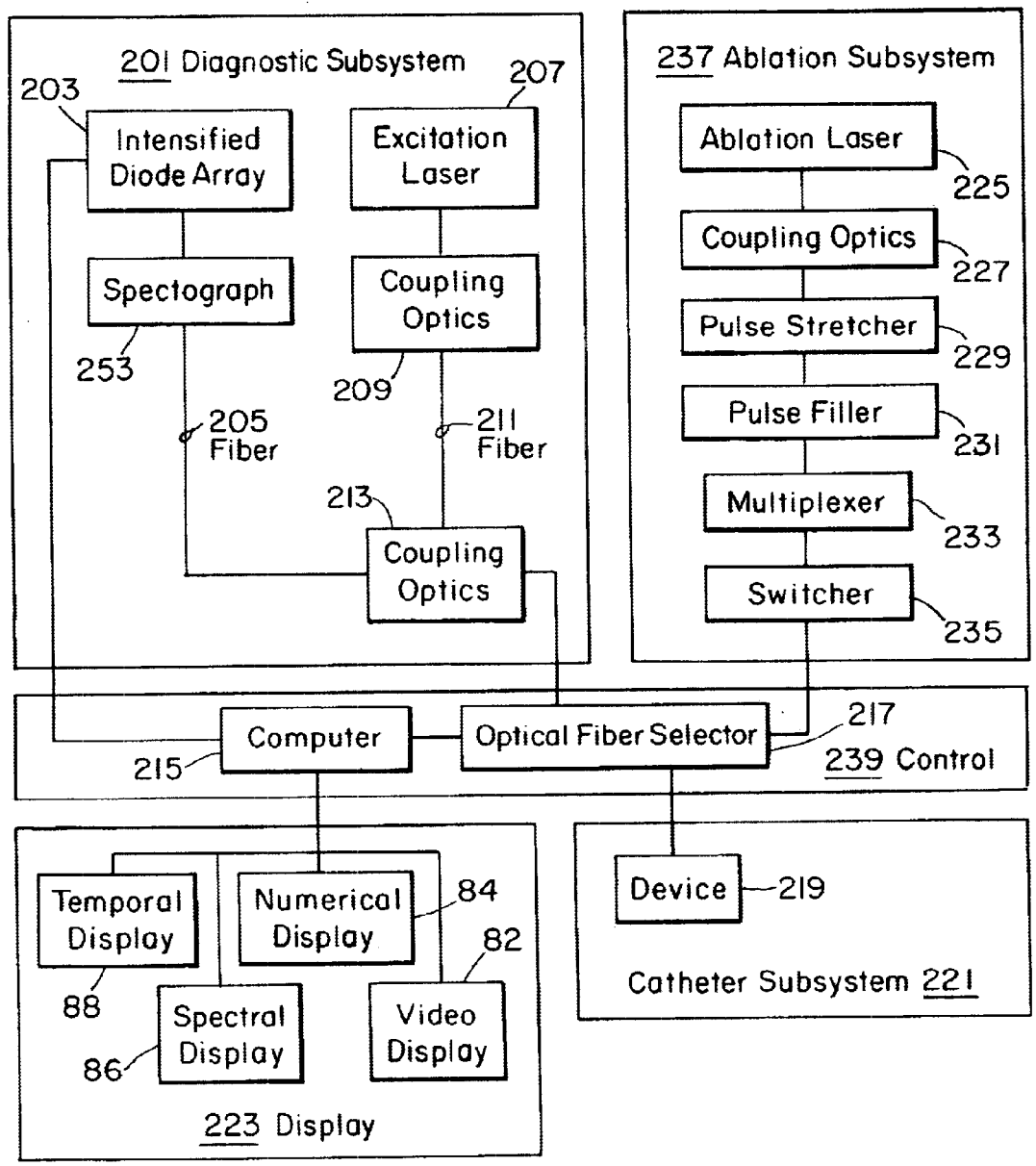
FIGS. 1A–1C are schematic illustrations of preferred systems for providing the spectroscopic measurements of the invention.

The spectroscopic methods of the present invention can be performed on a system such as that for laser treatment of atherosclerosis which is illustrated in FIG. 1A. FIG. 1A includes separate block diagrams for the system of the invention which utilizes laser light for spectroscopic diagnosis as well as for treatment and/or removal of tissue. The ablation laser 225, pulse stretcher 229 and the pulse filler/multiplexer 231, 233 produce an output laser ablation pulse of sufficient energy and intensity to remove tissue and sufficient pulse duration to propagate through a fiber optic laser catheter delivery system without damaging the fibers. These systems and methods are more fully described in co-pending application U.S. Ser. No. 07/644,202 filed on Jan. 22, 1991, U.S. Pat. No. 5,312,396, which is incorporated herein by reference.

Figure 1B:
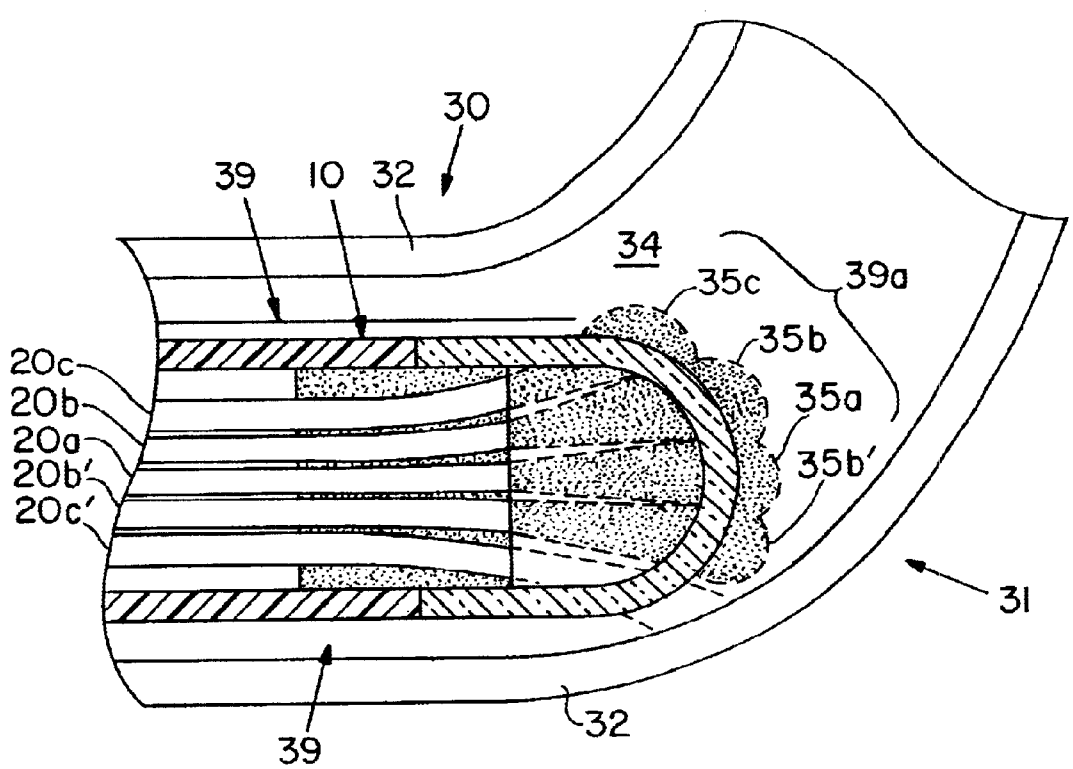

To remove plaque, a device 219 is used to contact the tissue such as multiple-fiber laser catheter 10 of FIG. 1B with an optical shield. The catheter 10 is inserted into the artery and the distal end of the catheter is brought into contact with the lesion. Next, a determination is made as to the type of tissue at which each optical fiber 20a–c' is aimed. Only fibers aimed at diseased tissue are activated. Thus, selective tissue removal is obtained. Furthermore, this technique is also applicable for guiding surgical procedures in other organs and tissue types such as the colon and bladder.

The present invention relates to systems and methods of performing spectral diagnostics to diagnose the tissue in front of each fiber. A preferred embodiment a laser light source 207 that is coupled to the fibers. The diagnostic light is sent to the fiber of choice by the optical fiber selector 217.

The diagnostic light exits the selected optical is fiber and falls on the tissue. The tissue absorbs the light and a fraction of the absorbed light is re-emitted, by Rayleigh fluorescence, Raman or other elastic or inelastic light scattering processes. This light is returned to the optical fibers and exits from selector 217, and is detected by a photodiode, photomultiplier or other detector 203. Returning light could use different optical fibers than those employed for illumination. Diagnostic subsystem produces the entire spectral signal which is coupled to computer 215.

The computer stores the information in a memory as a spectrum, which is a graph of light intensity vs. wavelength. This can be displayed immediately on the video display 82 or compared to an existing spectrum stored in the computer and the difference displayed on the spectral display 86. Temporal display 88 can display corrections made for the wavelength dependent sensitivities of the source. Information from either the temporal or spectral display can be stored in the computer 80. The comparative data is shown on numerical display 84 to provide a quantitative measure of the health of the tissue observed.

With a multichannel detector and a computer, or with appropriate multiple filters and detectors, it is possible to gather this information in a fraction of a second. Thus, a spectral or numerical display is provided which indicates the type of tissue at which the fiber of interest is aimed. If the tissue is plaque, and is to be removed, then fiber selector 217 will align this fiber with the output beam of the high power laser 225. Then, the high power laser 225 is turned on and an appropriate power level is selected for a predetermined amount of time to remove a certain amount of diseased tissue. The beam of laser 225 is transmitted to pulse stretcher 229 through coupling optics 227 and pulse filler/multiplexer 231, 233 to properly adjust the beam fluence.

The procedure is repeated for different fibers using switcher 235. Where diseased tissue is detected, it is quickly removed. The laser catheter 10 nibbles away at the plaque, leaving the healthy artery wall intact.

If the artery 30 makes a bend 31 as shown by FIG. 1B, the laser catheter 10 will tend to make contact with artery wall 32 at the outside wall of the bend. To prevent the catheter from contacting the artery wall, the optical fiber 20c is not fired. The lesion is removed asymmetrically. This allows the laser catheter 10 to follow the lumen 39, 39a around the bend. Thus, the artery wall 32 is not irradiated and is not perforated. Additional details of this fiber optic catheter 10 are disclosed in U.S. Pat. No. 4,913,142, the contents of which are incorporated herein by reference.

In both Raman and ATR methods, information is contained in the spectral lines which are observed in their intensities, and also their linewidths and center frequencies (and how they change in different environments). Further, Raman and infrared ATR have different "selection rules". Some vibrations seen in infrared ATR won't show up in Raman, and vice versa. In other cases the same vibration can be detected by both techniques, but with different relative intensities (e.g. a strong Raman line will be weak in ATR). So in this sense the two techniques provide complementary information and combining the two techniques (or using either or both with laser induced fluorescence) is valuable in diagnosing pathology.

The methods can utilize Fourier transform detection to observe the radiation thereby providing improved signal/noise ratios. Other techniques (e.g. diode array detection and CCD detection) can also be used.

As described in more detail below contributions from major tissue constituents can be "subtracted out" to reveal information about molecules which are present in small concentrations. For example, in ATR water contributions are removed before the "dry" tissue constituents could be studied. Also, derivative spectroscopy is used to eliminate background signals and low frequency filters. Note that these techniques deconvolute the observed spectra into its individual constituents, an essential step for optimal extraction of diagnostic information.

While Raman can sample deeply into tissue, ATR samples only a very thin layer (a few microns). Thus, ATR is "naturally" suited to probe surface disease, such as the superficial cancers of the bladder and GI tract, whereas Raman is well suited to providing information about conditions deep inside tissue (such as breast cancer or stones). This is important for 3D imaging. Furthermore, the ATR tissue sampling depth can be controlled by properly matching the probe surface material to the tissue type.

Generally, the ATR signal is very sensitive to the surface of the waveguide or probe. For example, if the probe surface has an affinity for lipids in the tissue, lipids can migrate to the probe surface, creating a thin lipid layer and producing a large signal. This can be a problem (it can give misleading information if not properly recognized and guarded against). Conversely, it can be used to advantage: Probes with special surfaces can be developed to prevent this effect or to promote it, in order to search for particular substances in the tissue.

In a preferred method one can adjust depth probed by ATR by varying refractive index of ATR probe. Alternatively as discussed below one can use a "waveguide needle" to get subsurface information.

Raman diagnostic methods permit adjustment of Raman depth by varying the wavelength. Penetration depth is wavelength dependent, and can be varied by choosing different excitation wavelengths between about $\lambda=700$ nm and 2 $\mu$m. Another potentially important way of adjusting Raman depth is to vary the collection angle. In the near IR, incident (exciting) light is strongly scattered out of the forward direction into larger angles, so Raman signals sampled at smaller angles come from tissue closer to the surface. Therefore, the Raman sampling depth can be controlled to a large extent by probe design.

Depth information is important if one desires to provide imaging by creating 3D images of small tumors in the brain or breast. Differential techniques based on the ideas of the preceding paragraph might allow accurate localization of such tumors in three dimensions. Near-IR Raman can be combined with a sound wave technique (time of flight or standing waves setup in the tissue)—the sound wave would modulate the Raman signal emanating from a point in the tissue when it passes that point, and the modulated signal could be used to establish the depth of the tissue producing the signal.

Figure 1C:
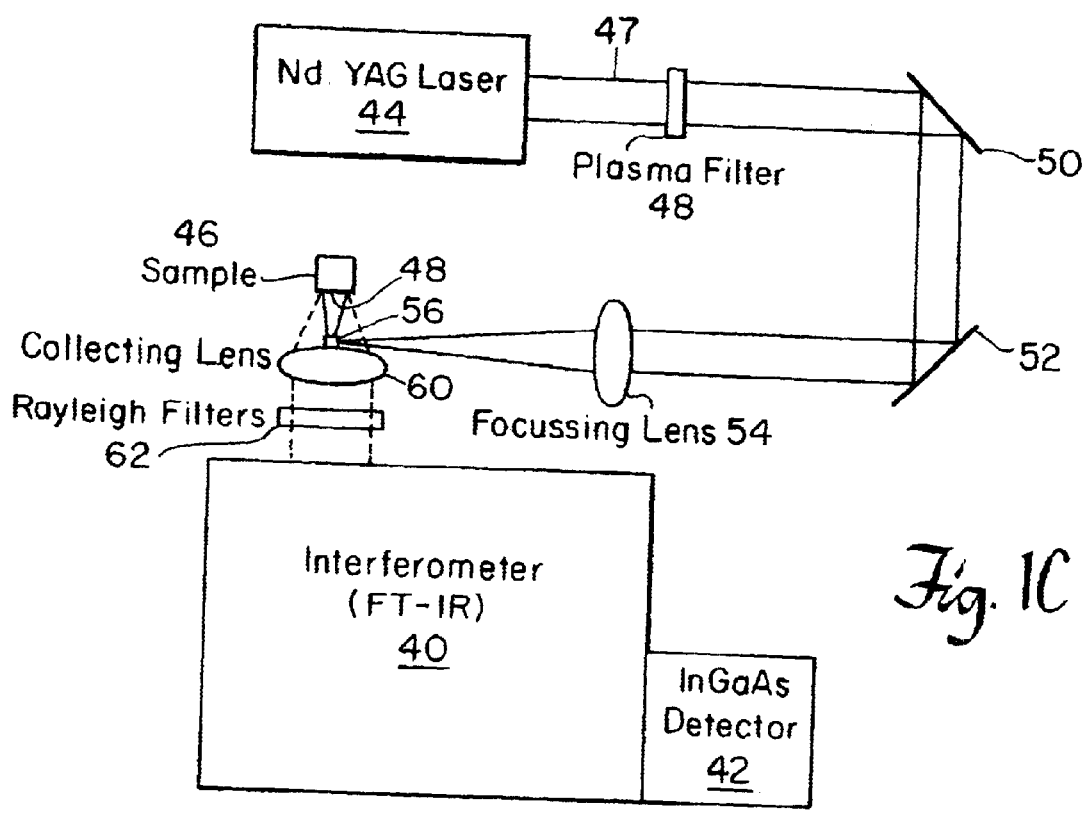

A system employed for the collection of Raman spectral data from excised tissue samples is illustrated in FIG. 1C. FT-Raman spectra were measured from 0–4000 $cm^{-1}$ below the laser excitation frequency with a FT-IR interferometer 40 equipped with a FT-Raman accessory. The accessory employed at 180 back scattering geometry and a cooled (77 K) InGaAs detector 42.

A 1064 nm CW Nd:YAG laser 44 can be used for irradiating a sample 46: utilizing 500 mW to 1 W laser power in a 1.0 to 2.5 mm spot 48 at the sample 46 to collect Raman data. Alternatively, a pulsed laser source can also be employed. Laser 44 generated a beam 47 that is directed through plasma filter 48, mirrors 50, 52, focussing lens 54 and mirror or prism 56 before irradiating the sample 46. The radiation received by sample 46 undergoes various mechanisms of absorption, reflection and scattering including Raman scattering. Some of the light emitted by the tissue is directed toward lens 60 and then through one or more Rayleigh filters 62. The collecting lens 60 collects this backscattered light 64 and collimates it. The Rayleigh filters 62 removes the elastically scattered light and transmits the inelastically scattered, frequency shifted (Raman) light. The Raman scattered light enters the interferometer 40. No visible sample degradation was observed under these conditions.

Excised human aorta was chosen of atherosclerotic artery tissue. Samples were obtained at the time of post mortem examination, rinsed with isotonic saline solution (buffered at pH 7.4), snap-frozen in liquid nitrogen, and stored at −85 C until use. Prior to spectroscopic study, samples were passively warmed to room temperature and were kept moist with the isotonic saline. Normal and atherosclerotic areas of tissue were identified by gross inspection, separated, and sliced into roughly 8×8 mm pieces.

The tissue samples were placed in a suprasil quartz cuvette with a small amount of isotonic saline to keep the tissue moist, with one surface in contact with the irradiated by the laser 44. The spectra shown in FIGS. 2 through 6 were collected with 512 scans at 8 $cm^{-1}$ resolution (approximately 35 minutes total collection time).

Human aorta is composed of three distinct layers: intima, media, and adventitia. The intima, normally less than 300 $\mu$m thick, is the innermost layer and provides a non-thrombogenic surface for blood flow. It is mainly composed of collagen fibers and ground substance. The medial layer, typically about 500 $\mu$m thick, is quite elastic and serves to smooth the pulsatile blood flow from the heart. The structural protein elastin is the major component of aortic media, with some smooth muscle cells present as well. The outermost adventitial layer serves as a connective tissue network which loosely anchors the vessel in place, and is mainly made up of lipids, lipoproteins and collagen. During the atherosclerotic process, the intima thickens due to collagen proliferation, fatty necrotic deposits accumulate under and within the collagenous intima, and eventually, calcium builds up, leading to calcium hydroxyapatite deposits in the artery wall.

Figure 2:
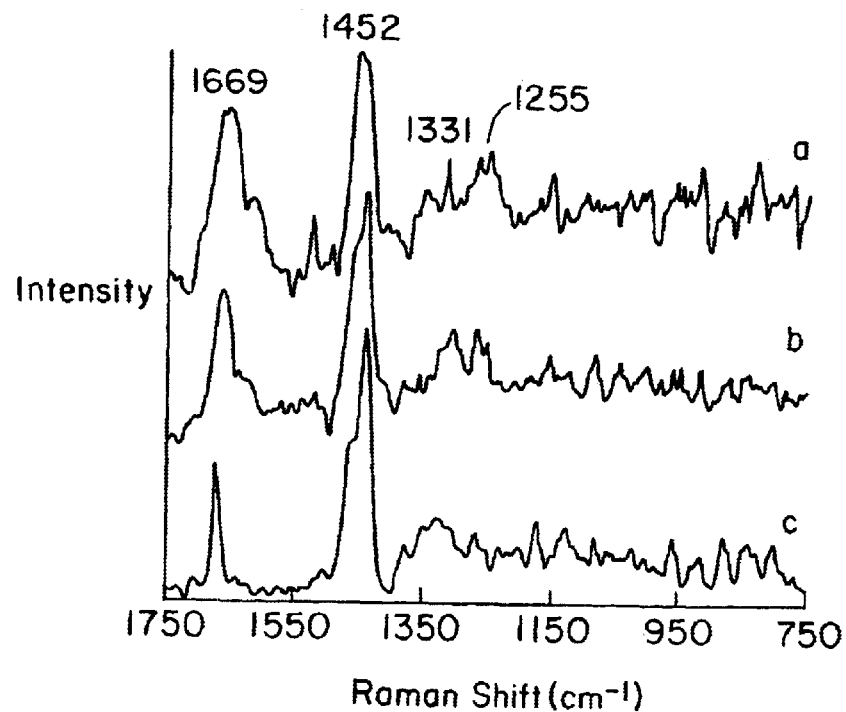
FIG. 2 graphically illustrates FT-Raman spectra of human aorta: a) normal artery; b) atheromatous plaque; c) FT-Raman spectrum solid cholesterol (Sigma).

FIG. 2, curve a, shows the FT-Raman spectrum of a full thickness section of aorta grossly identified as normal. Laser irradiation was on the intimal side. The dominant bands appear at 1669 $cm^{-1}$ and 1452 $cm^{-1}$ and can be assigned to an amide I backbone and C—H in-plane bending vibration from proteins, respectively. Weaker bands at 1331 and 1255 $cm^{-1}$ are assigned to C—H wagging and amide III vibrations from proteins, respectively. The frequencies of amide I and III are consistent with those observed for disordered proteins.

Figure 3:
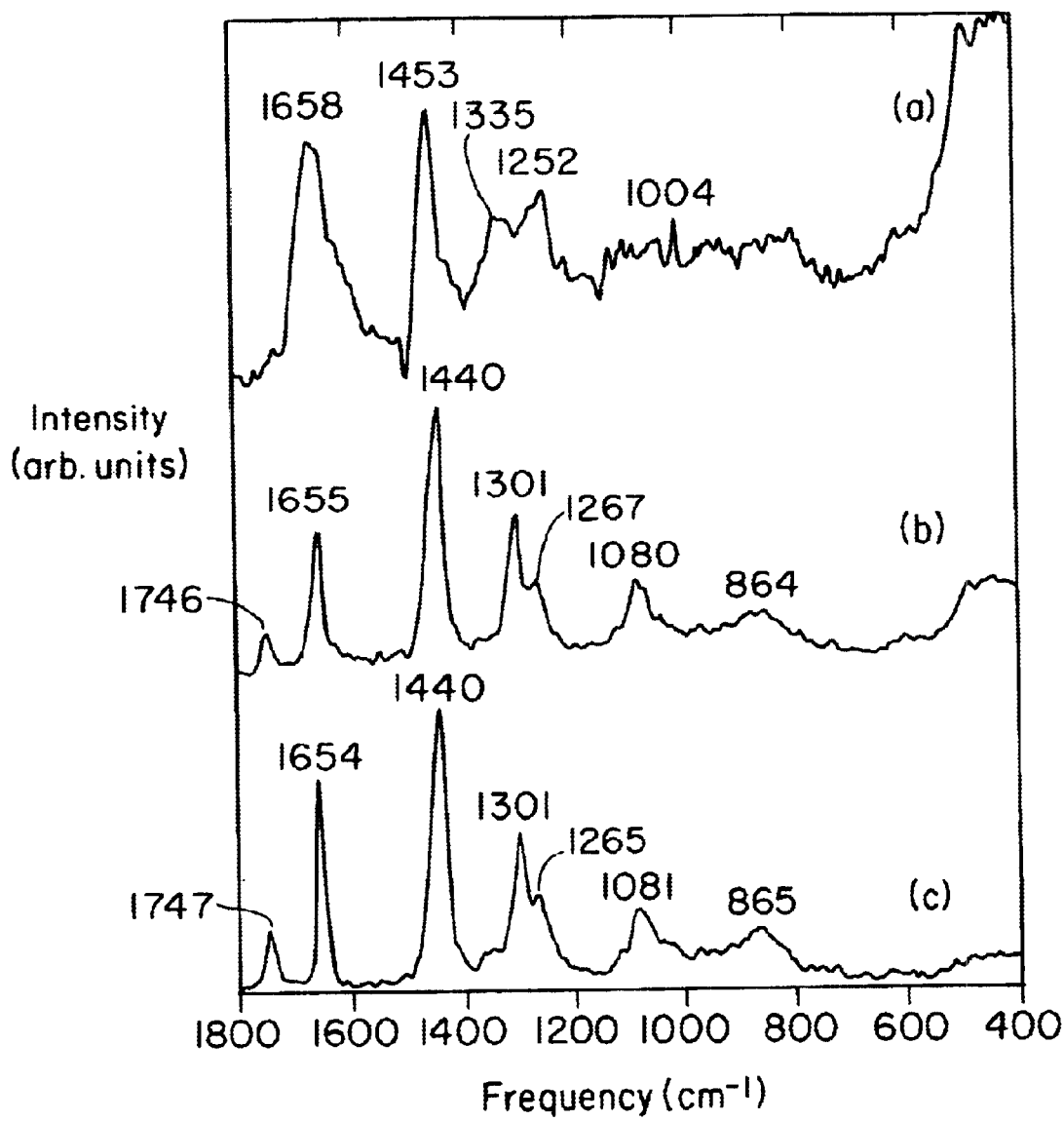
FIG. 3 graphically illustrates FT-Raman spectra of normal human aorta: a) irradiated from intimal side (spectrum multiplied by 3); and b) irradiated from adventitial side (primary adipose tissue). c) NIR FT-Raman spectrum of triglyceride, triolein.

Another example of a typical NIR FT Raman spectrum from normal aorta is shown in FIG. 3. When irradiated from the intimal side, FIG. 3, curve a, the major vibrational bands observed in normal aorta are all attributable to protein vibrations: the band at 1658 $cm^{-1}$ is assigned to the amide I vibration of the polypeptide chain, the 1453 $cm^{-1}$ band to a C—H bending mode of proteins, and the 1252 $cm^{-1}$ band to the amide III vibration. The spectrum of normal aorta is at least 25% weaker than any of the pathologic samples. The peak frequency of the C—H bending band, which averaged for all the normal specimens is 1451±1 $cm^{-1}$, is specific to the protein C—H bending mode (See below). The weak band near 1335 $cm^{-1}$, which appears as a shoulder in many of the normal specimens, appears to be specific to elastin, and the weak band at 1004 $cm^{-1}$ is likely due to phenylalanine residues. In general, the relative intensities of the bands in the region between 1250 and 1340 $cm^{-1}$ appears very much like that observed in the FT Raman spectrum of elastin. This observation is consistent with the thin collagenous intima in normal aorta, the elastic nature of the media of aorta, and the deep penetration depth of 1064 nm radiation. Band assignments for all tissue types presented here are listed in Table 2.

FIG. 3, curve b, displays the NIR FT Raman spectrum of the adventitial side of normal aorta. In this case, the irradiated adventitial surface consisted of several millimeters of visible adipose tissue. In contrast with the spectrum collected from the intimal side, the bands observed in this adipose material appear to be mainly due to lipid, and in particular triglyceride, with almost no contribution from protein. This is not unexpected, as the triglyceride content of adipose tissue is on the order of 60%. The sharp band at 1655 cm$^{-1}$ is due to stretching of C=C groups in unsaturated fatty acid chains. This band is distinguished from amide I by its peak frequency and its width, which in this case is 17 cm$^{-1}$ FWHM. Amide I, in contrast, is roughly 60 cm$^{-1}$ wide. The dominant C—H bending band is shifted to 1440 cm$^{-1}$, characteristic of lipids. This band is about 3 times more intense in adipose tissue than in normal intima, probably a result of the greater number of C—H groups per unit volume in triglycerides. The bands as 1301/1267 cm$^{-1}$ and 1080 cm$^{-1}$ are assigned to C—H bending and C—C stretching vibrations of fatty acids, respectively.

The 1746 cm$^{-1}$ band, assigned to the C=O stretching mode of the triglyceride ester linkages, indicates that most of the lipid observed in the adventitial adipose tissue is of the triglyceride form. Specifically, the integrated intensity of this band relative to the C—H bending band at 1440 cm$^{-1}$ is equal to 0.103, while this same ratio for triolein is 0.136, which indicates that roughly 75% of the C—H band is due to triglyceride. The NIR FT Raman spectrum of triolein (a triglyceride containing fatty acid chains of 18 carbons and a single double bond) is shown for comparison in FIG. 3, curve c. Additional molecular information regarding the state of the fatty acid chains is readily deduced from the adventitial adipose spectrum. For example, the relative intensity of the C=C band at 1655 cm$^{-1}$ indicates that there are on average roughly 0.7 unsaturated double bonds per fatty acid chain, assuming 16–18 carbon fatty acids. In addition, the frequencies and structures of the C—H bending and C—C stretching bands suggest that most of the fatty acid chains are in the gauche conformation. The sharp 1129 cm$^{-1}$ band, characteristic of all-trans chains, is not observed in the spectrum.

The FT-Raman spectrum obtained from a diseased artery, an atheromatous plaque, with a thick fibrous connective tissue cap and an underlying necrotic core is shown in FIG. 2, curve b. The necrotic core of an atheromatous plaque contains cellular debris as well as large accumulations of oxidized lipids and cholesterol. The band in the amide I region, peaking at 1665 cm$^{-1}$, is distinctly narrower in this spectrum compared to normal aorta. In addition, the in-plane C—H bend, at 1444 cm$^{-1}$, is relatively more intense and has a distinct shoulder at higher frequency. The two weaker bands at 1307 and 1267 cm$^{-1}$ are shifted in frequency from those found in the spectrum of normal aorta. The band frequencies and shapes in the FT-Raman spectrum of cholesterol, shown in FIG. 2, curve c, coincide with some of those observed in the atheromatous plaque, consistent with the expected composition of the necrotic core.

Figure 5:
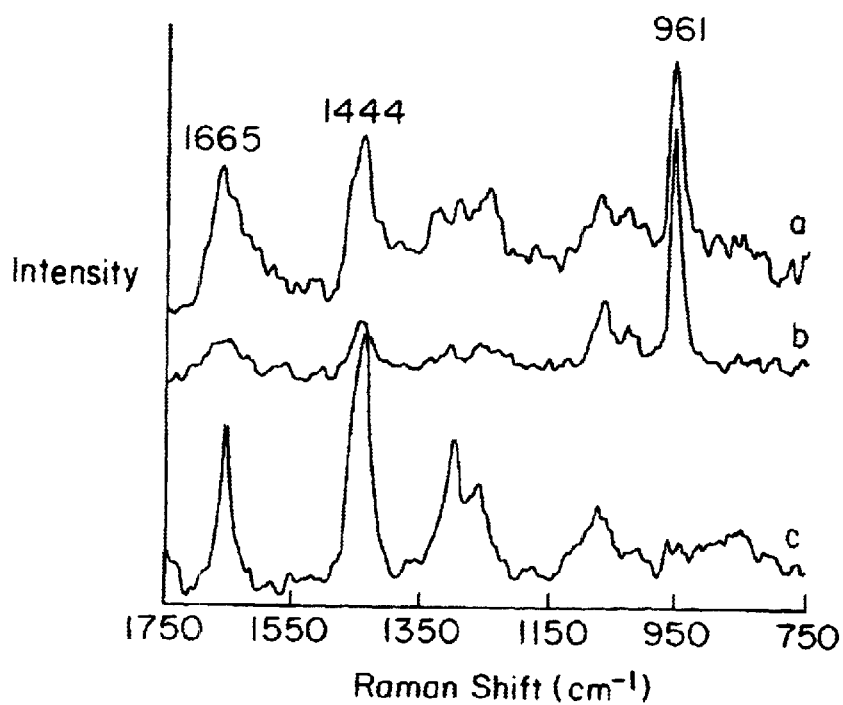
FIG. 5 graphically illustrates FT-Raman spectra of calcified human aorta: a) calcified with fibrous cap; b) excised calcification from a different plaque; c) spectra of the same tissue as in a) taken from adventitial side.
Figure 4:
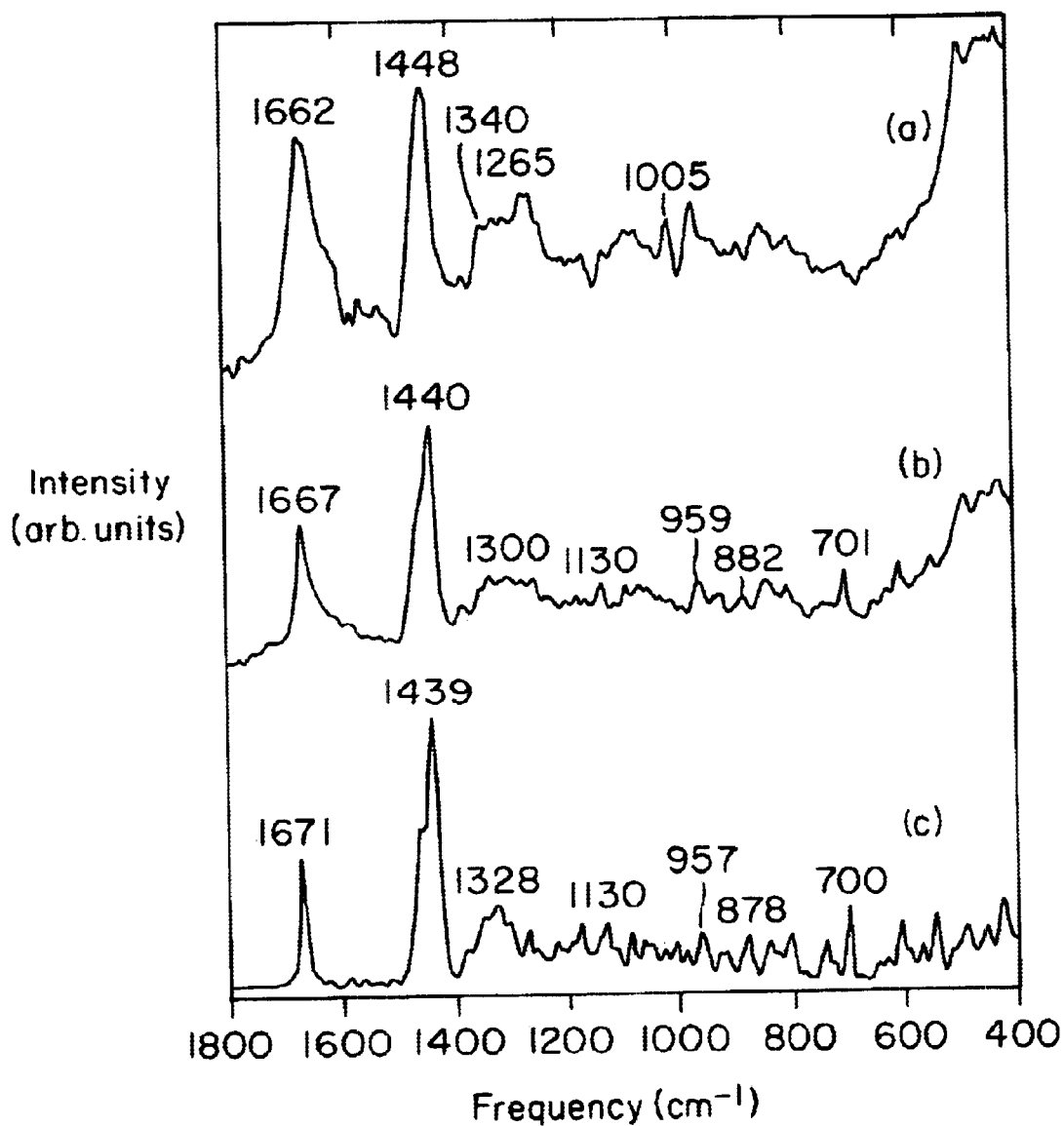
FIG. 4 graphically illustrates FT-Raman spectra from human aorta: a) fibrous plaque; and b) atheromatous plaque. c) FT-Raman spectrum of cholesterol monohydrate powder.

The NIR FT Raman spectra of other fibrous plaque specimens exhibit a range of features as shown in FIGS. 4 and 5. FIG. 4, curve a, shows a representative spectrum from one of the types of fibrous plaques. These fibrous plaque spectra are quite similar in both relative and absolute band intensities to the spectra of normal aorta. The most significant differences are that the C—H bending band, peaking near 1448 cm$^{-1}$ on average, is shifted by 2 cm$^{-1}$ to a slightly lower frequency. This may be the result of a small increase in the lipid content of these plaques relative to normal aorta. In addition, the band near 1340 cm$^{-1}$, attributed to elastin in normal aorta, is decreased relative to amide III at 1265 cm$^{-1}$. The putative explanation is that the collagenous intima is thickened in these specimens, so that the spectral contribution from the elastic media is reduced relative to that of normal aorta.

The NIR FT Raman spectra of other fibrous plaque specimens appeared similar to atheromatous plaques' spectra (FIG. 2, curve b,). These are substantially different than either normal aorta, or adipose tissue. In these cases, the intense C—H bending band occurs at 1440 cm$^{-1}$, characteristic of lipid material. This band is roughly twice as intense as the C—H bending band in normal aorta. The complete absence of a band at 1746 cm$^{-1}$ indicates that this lipid is not triglyceride. In fact, this lipid appears to be predominantly cholesterols, as identified by the sharp, characteristic band at 700 cm$^{-1}$ and comparison to the cholesterol spectrum shown in FIG. 4, curve c. Again, this is not surprising, since cholesterols accumulate in high concentrations in atherosclerotic lesions. Several of the bands between 1000 and 500 cm$^{-1}$ are assignable to vibrational modes of the sterol rings. These include the bands at 959, 882, 844, 805, 700, 605, and 546 cm$^{-1}$. In addition, the 1666 cm$^{-1}$ band is attributed in part to the C=C stretching vibration of the steroid nucleus.

The presence of fatty acid chains in the atheromatous plaque spectra is evidenced by bands at 1300/1262 cm$^{-1}$ and 1130/1088 cm$^{-1}$, due to C—H bending and C—C stretching vibrations, respectively. These bands may contain contributions from cholesterol as well. The relative intensities of the fatty acid band at 1300 cm$^{-1}$ and the sterol ring bands suggest a mixture of free cholesterol and cholesterol-fatty acid esters. Moreover, the relative intensities of the 1130 cm$^{-1}$ C—C stretching and the 700 cm$^{-1}$ sterol bands indicate that most of the fatty acid chains are in the gauche conformation, consistent with the predominance of unsaturated fatty acid chains in the cholesterol esters in these plaques. It is particularly noteworthy in the atheromatous plaques that the cholesterol deposits are detected from material below a thick fibrous cap indicating the ability of the NIR FT Raman method to probe materials several hundred microns below the tissue surface.

In addition to the cholesterol and cholesterol ester bands, the NIR FT Raman spectra of some of the fibrous plaques contained two unique bands, at 1519 and 1157 cm$^{-1}$. The intensities of these bands are highly correlated, which suggests that they are due to a single component. These bands, which have been previously observed in visibly-excited Raman spectra of atherosclerotic plaques, are assigned to carotenoids. The amount of carotenoid in these plaques is probably much smaller than the amounts of cholesterols or proteins, but may be strongly pre-resonance enhanced (14). The carotenoid bands are observed only in this subset of fibrous plaques.

Figure 6:
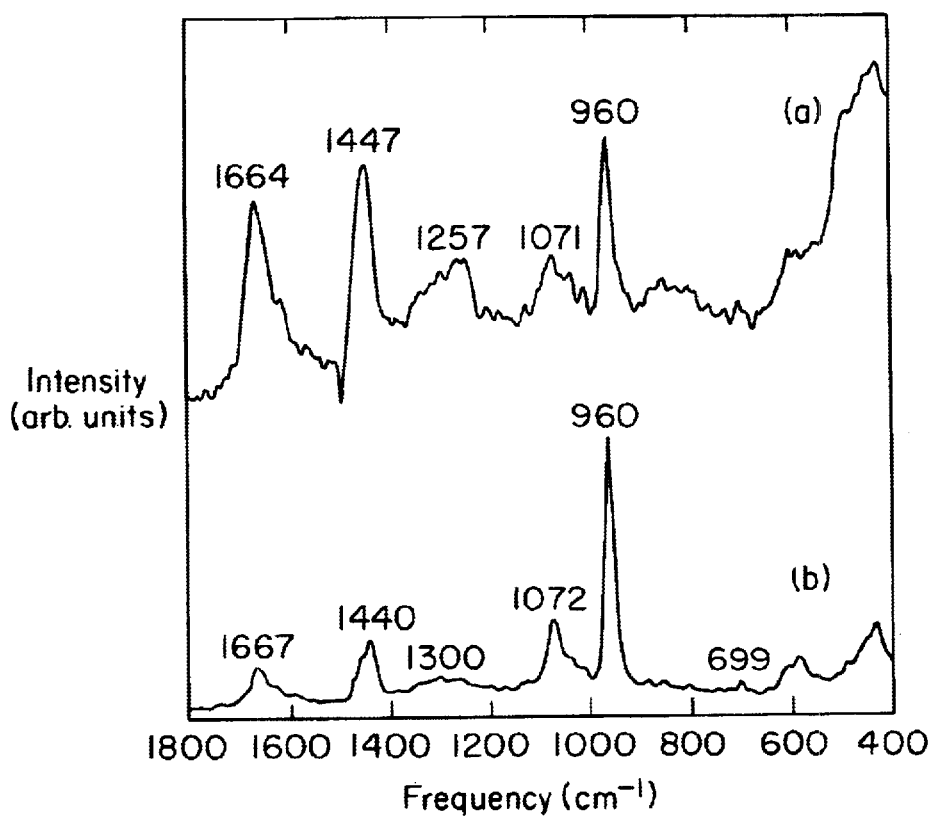
FIG. 6 graphically illustrates FT-Raman spectra of calcified human aorta: a) calcified plaque with a fibrous cap (spectrum multiplied by 8); and b) exposed calcification.

In an advanced plaque, calcium may begin to accumulate leading to the formation of calcium hydroxyapatite crystals in the tissue as shown by the spectra of FIGS. 5 and 6. The FT-Raman spectrum of a calcified plaque with a thick (several hundred microns) fibrous connective tissue cap overlying a calcified deposit is shown in FIG. 5, curve a. The spectrum clearly indicates bands due to the protein in the fibrous cap, amide I and III at 1665 and 1255 cm$^{-1}$, respectively. However, additional bands are observed between 1250 and 1350 cm$^{-1}$ and around 1100 cm$^{-1}$, as well as a strikingly sharp band at 961 cm$^{-1}$. The latter is readily assigned to the symmetric phosphate stretching vibration associated with phosphate groups in the calcium hydroxyapatite deposits, while the band around 1100 cm$^{-1}$ is an asymmetric phosphate stretch. These assignments are confirmed by excising the solid "rock" from a different calcified plaque, and obtaining its spectrum as shown in FIG. 5, curve b. A strong Raman signal from the phosphate stretching vibration in solid calcifications in advanced atherosclerotic plaques can also be observed utilizing standard visible Raman instrumentation. The ability to detect the calcifications several hundred microns below the tissue surface when using near IR FT-Raman spectroscopy, however, is a diagnostic measurement which can be utilized to guide treatment.

A measurement was attempted to determine if the calcification might be detected when the tissue was irradiated from the adventitial side. The resulting FT-Raman spectrum is shown in FIG. 5, curve b,. No evidence of the strong phosphate vibration is apparent. In contrast, sharp vibrational bands at 1745, 1656, 1444, 1303, 1267 and 1082 $cm^{-1}$ are observed which are mainly associated with the lipid material that constitutes the majority of the adventitia.

The NIR FT Raman spectrum of calcified plaque, containing a subsurface calcified deposit and an overlying soft fibrous cap, exhibits an intense, sharp, new band at 960 $cm^{-1}$ (FIG. 6, curve a,). This band, specific to calcified tissue, is assigned to the symmetric stretching vibration of phosphate groups (15), which are present in high concentrations in the solid calcium salts. The weaker phosphate antisymmetric stretch is also present at 1072 $cm^{-1}$. A symmetric stretching vibration of carbonate groups may also contribute to this latter band. The phosphate vibrations are easily observed from subsurface deposits in the calcified plaques: the 960 $cm^{-1}$ band can be observed from deposits up to 1.5 mm beneath a soft tissue cap with the current signal-to-noise level (See below). The calcified plaque also displays protein vibrations from the fibrous tissue cap. These include amide I at 1664 $cm^{-1}$ and amide III near 1257 $cm^{-1}$. The C—H bending band at 1447 $cm^{-1}$ suggests a mixture of protein and lipid, and the weak band at 699 $cm^{-1}$ is likely due to cholesterol that is either in the fibrous cap, the calcified deposit, or both.

The NIR FT Raman spectra of exposed calcifications (FIG. 6, curve b,) display a range of features. In all cases, the major bands are due to the calcium salts. These include the 960 $cm^{-1}$ phosphate and 1072 $cm^{-1}$ phosphate/carbonate bands as well as the band at 587 $cm^{-1}$, which is assigned to another phosphate vibrational mode. On the other hand, several differences are apparent in the weaker bands, which are presumably due to soft tissue components which are embedded in the calcification. In some cases (not shown), the C—H bending band occurs at 1450 $cm^{-1}$, and the band at 1663 $cm^{-1}$ is similar in shape to amide I for some of the calcifications, indicative of protein vibrational modes. In other calcified plaques, such as that in FIG. 5, curve b, the C—H bending band occurs at 1440 $cm^{-1}$, and the 1667 $cm^{-1}$ band, which is much sharper, is more like due to c=c stretching vibrations. In this plaque, the bands are due to lipid, in particular cholesterols, as evidenced by the 700 $cm^{-1}$ and 1300 $cm^{-1}$ bands.

In our histological examinations of aorta, two distinct types of exposed calcifications have been noted. In one type, the fibrous tissue cap is calcified. In the other, the necrotic core of an atheromatous plaque is calcified, and the calcified deposit is exposed by ulceration of the soft tissue fibrous cap. A positive explanation for the two spectral types of exposed calcifications is that the specimens which exhibit protein bands are of the former histologic type, while the specimens which exhibit lipid bands are of the latter type.

The present methods provide an IR FT-Raman technique for differentiating various stages of atherosclerosis in human aorta. They demonstrate that molecular level information is available using these methods. This information is useful for following the pathogenesis of the disease and in guiding the treatment of different lesions. The near IR FT-Raman method, with its relatively deep penetration depth, is able to obtain spectroscopic signals from below the tissue surface, yielding details about the atheromatous necrotic tissue and sub-surface calcifications. These signals can be utilized with an optical fiber based imaging system to determine the content and composition of different atherosclerotic plaques in vivo.

Figure 7:
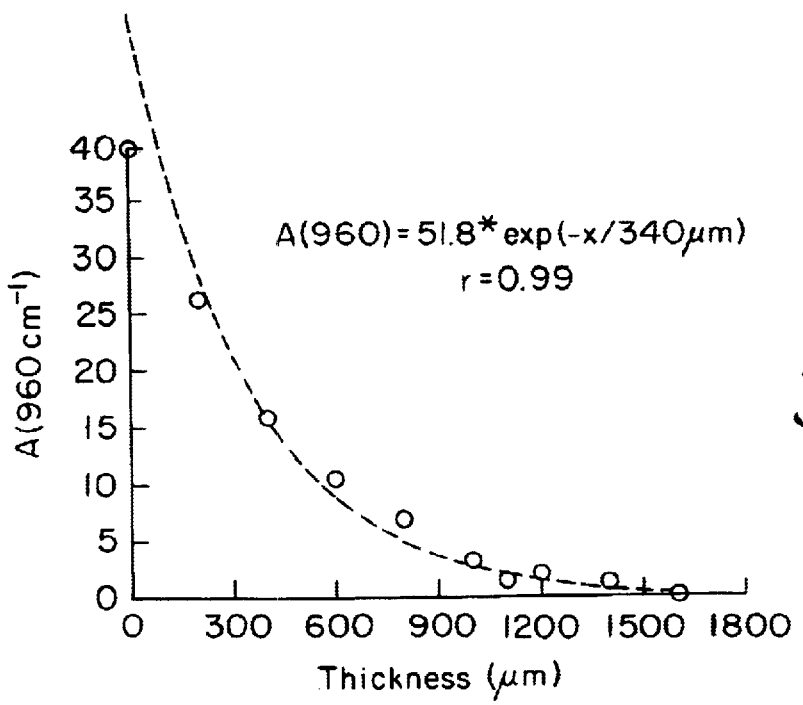
FIG. 7 graphically illustrates the measured NIR Raman intensity of the 960 cm band ($A(960\ cm^{-1})$) indicates the area of this band) in a calcified deposit as a function of depth below the irradiated surface. The dashed curve corresponds to the fit of an exponential function to the data with an exponent of 2.94 $mm^{-1}$.

With the observation that several of the biochemical species important in the atherosclerotic process, including cholesterol and calcium hydroxyapatite, can be easily detected below the tissue surface, we wished to determine the depth limit of detection using the NIR FT Raman technique. In order to address this question, ten 200 $\mu$m sections of aortic media were cut and placed one at a time over a large calcified deposit (6×6×3 mm), and the FT Raman spectra of the 960 $cm^{-1}$ band monitored as a function of depth below the surface. As indicated by the plot of FT Raman intensity versus depth shown in FIG. 7, the signal from the calcified deposit was detectable until the deposit was greater than 1.6 mm below the irradiated surface. Even slightly deeper depths could be probed if the focus of the collection optics was moved into the tissue.

The two dimensional resolution of the NIR FT Raman signal for material below the tissue surface was then tested by placing 1 mm of aortic media above another calcified deposit, and moving the tissue transversely in two dimensions through the laser beam and collection lens. The FT Raman signal was observed to drop-off rapidly as the beam and collection optics moved from the calcified deposit. The detected FT Raman signal closely followed the geometry of the calcified deposit below the surface, despite the significant scattering of the overlying layer of tissue. This result suggest that the Raman scattered light may be utilized for imaging objects below the tissue surface with minimal image blurring due to elastic scattering in the tissue.

A second spectroscopic method is also used to obtain molecular vibration information, attenuated total reflective (ATR) of infrared light.

Human aorta was chosen as an example to illustrate the diagnosis of atherosclerotic artery tissue. As in the samples obtained for the Raman spectral measurements human aorta samples were obtained for ATR measurements at the time of post mortem examination. Sample storage and preparation procedures are identical to those set forth for the Raman spectral measurements. These reflectance measurements can be used by themselves to provide diagnostic data in conjunction with either the Raman spectroscopic measurements described above or with fluorescence measurements, or with both types of measurements to enhance diagnosis for specific applications.

The medial layers of a normal arteries and the necrotic cores of atheromatous plaques were exposed by blunt dissection and spectroscopically examined. ATR spectra were also collected from several purified tissue components including collagen, elastin, and cholesterol to assist in analysis of the spectra.

Mid-infrared ATR spectra were measured from 4000 to 700 $cm^{-1}$ with a commercially available FT-IR spectrometer and a horizontal ATR accessory. The sampling area was purged with dry nitrogen gas to control background absorption from atmospheric water vapor and $CO_2$. Spectra were collected at 4 $cm^{-1}$ resolution with 50 scans. The artery specimens, kept physiologically moist with isotonic saline (buffered at pH 7.4), were placed in contact with the ATR element (ZnSe crystal 45 ends). A 5 gram weight placed on the tissue sample ensured uniform sample contact with the ATR element. An ATR spectrum of the saline solution with absorbance similar to that of the artery samples was also obtained and used for subtraction of spectral components due to water. Collagen (Calbiochem: type I, bovine achilles tendon) and elastin (Sigma: bovine neck ligament) were prepared as saline slurries. Cholesterol (Sigma) was prepared as a dry film on the ATR element by evaporation of a benzene solution. These elements can be clearly identified in the resulting spectra.

The ATR sampling crystal is a rod of high refractive index material which acts as a waveguide for the infrared sampling beam. This waveguide can be in the form of a needle that is adapted for penetration into the tissue to be diagnosed. Alternatively, the probe will have a geometry suitable for contacting the surface of exposed tissue sites or for contacting internal locations with a catheter.

Figure 16A:
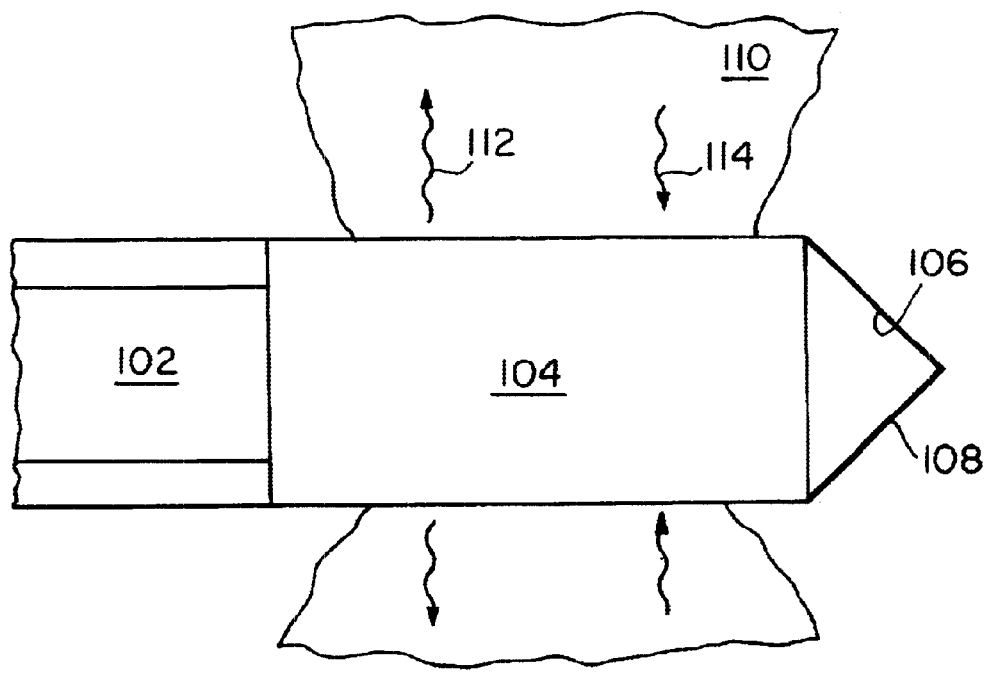
FIGS. 16A and 16B are additional preferred embodiments of ATR probes adapted to make the diagnostic measurements of the present invention.
Figure 16B:
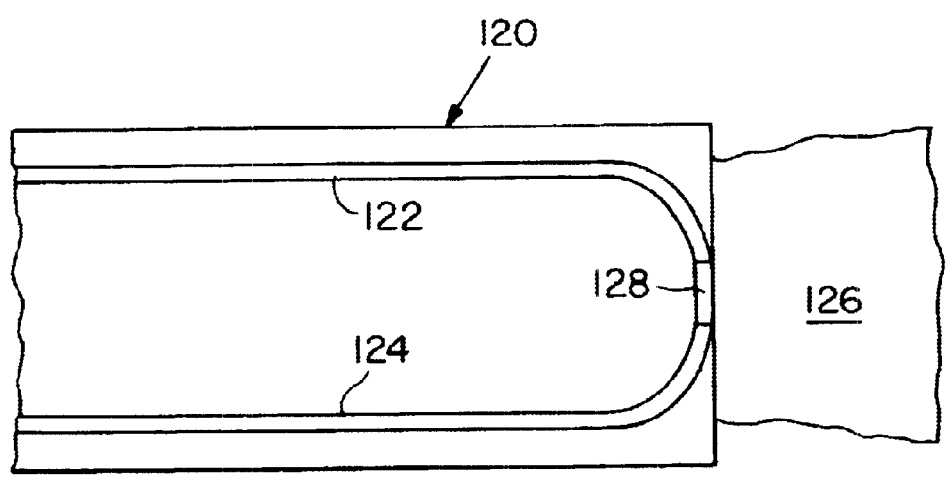

The devices shown in FIGS. 16A and 16B illustrate preferred embodiments of the invention adapted for ATR diagnostic measurements within the human body. In FIG. 16A a single-ended probe 100 is shown where one or more optical fibers 102 both the incident light to, and the transmitted (reflected) light from, the ATR element 104. A 100% infrared reflector 106 such as gold is placed at the distal surface 108 of the ATR element 104 functions to return the transmitted light back through the same fiber as well as to provide double pass sampling. The ATR element 104 can be a separate component optically fastened to the optical fibers 102, or alternatively, it can be constructed from the end of the optical fiber by removing the cladding material. Sampling is provided by placing the ATR element in contact with the tissue 110 of interest. Radiation is transmitted 112 and collected 114 in a radial direction from element 104. The probe can either be inserted through a standard endoscope or catheter to sample a hollow organ, or, if made with sufficiently thin optical fiber, it can be directly inserted directly into a solid organ as in the case of needle biopsy. In this particular embodiment the distal tip 108 is in the form of a needle. The cone or needle configuration on the end of the catheter can be long or shallow.

A double-ended probe is illustrated in FIG. 16B. Incident IR beam from FT-IR is transmitted through IR optical fiber 122 to ATR element 128 positioned at the distal end of catheter body 120. The ATR element is placed in contact with tissue 126 surface to be sampled. Transmitted light is conducted through a second IR optical fiber 124 back to an IR detector. The ATR element may be a separate component optically fastened to the two optical fibers 122, 124, or it may be simply a region of a single optical fiber in which the fiber cladding material has been removed. The entire apparatus can be inserted through a standard endoscope or outer catheter.

For methods of measuring excised samples, the specimen to be sampled is placed in optical contact with the surface of the waveguide or ATR element. The evanescent wave which extends outside of the waveguide surface is absorbed by the sample in proportion to its absorption coefficient. The penetration depth of the evanescent wave into the sample depends on the wavelength of the infrared radiation and the refractive indices of the waveguide and the sample; for a ZnSe-water interface, this depth is roughly 1 $\mu$m from 1800 to 700 $cm^{-1}$. The 1/e penetration depth of the evanescent wave into the sample is given by $\lambda/2\pi(n_z^2\sin^2\theta - n_w^2)^{1/2}$, where $\lambda$ is wavelength, $\theta$ is angle of incidence and $n_z$ and $n_w$ are the refractive indices of ZnSe and water respectively. Consequently, only tissue that is in good optical contact with the ATR element will be sampled. In addition, individual components in the sample can exhibit different affinities for the waveguide material (ZnSe in this case), which can influence the relative concentrations of the components at the waveguide surface. Despite relatively high concentrations in the bulk tissue, components with poor optical contact can be difficult to measure in the ATR spectrum.

Figure 8:
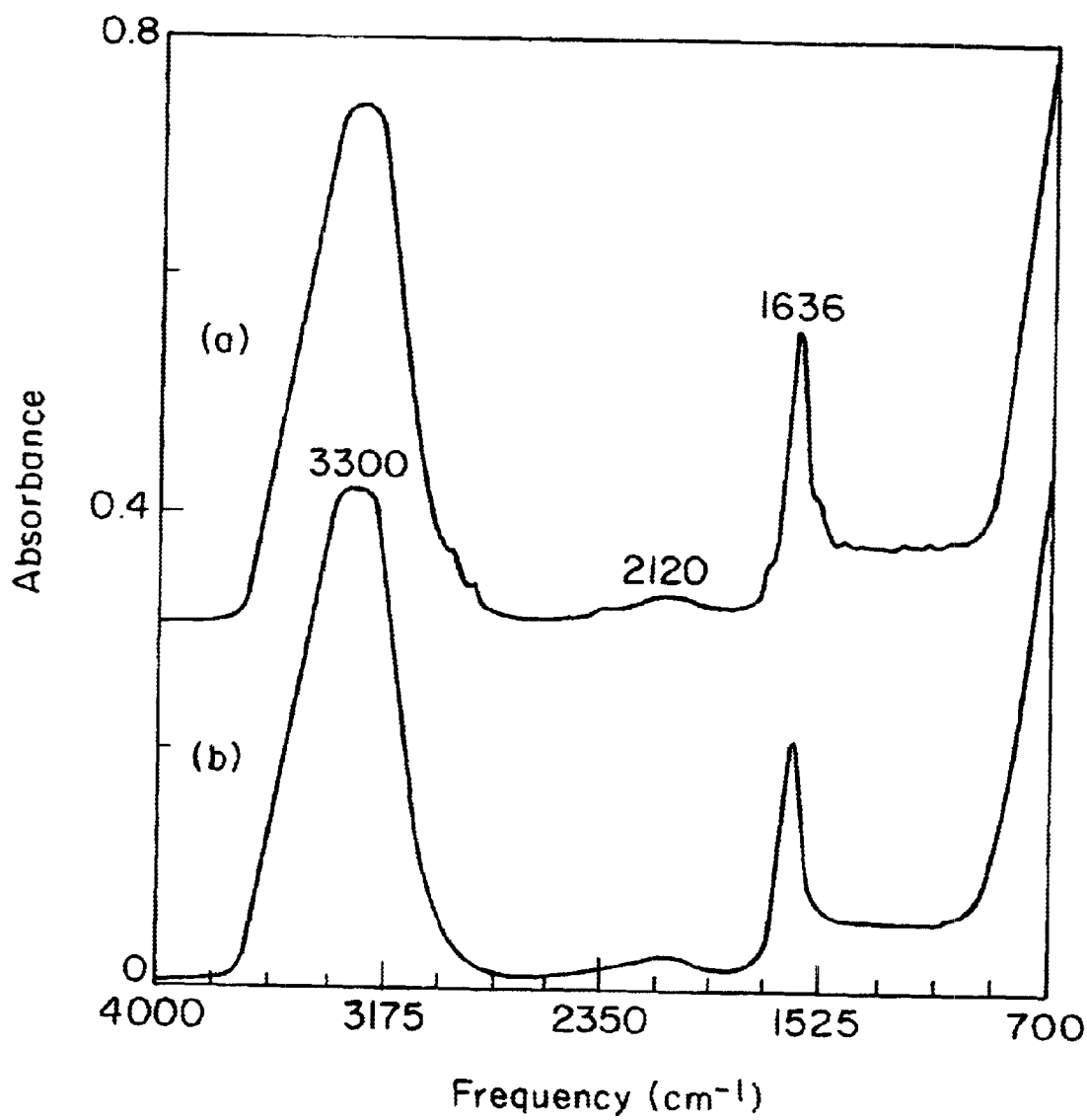
FIG. 8 graphically illustrates FT-IR ATR spectra (4000–700 $cm^{-1}$) of (a) normal aorta, intimal surface; and (b) buffered saline (0.14 M NaCl,pH 7.4).

FIG. 8 shows FT-IR ATR spectra of (a) normal aorta (intimal side) and (b) buffered saline. A comparison of these spectra shows that a majority of the IR absorption of normal intima can be attributed to water, which comprises roughly 80% of the tissue by weight. The large, broad bands peaking at 3300 $cm^{-1}$ and 1636 $cm^{-1}$ are due to the O—H stretching and H—O—H bending vibrations, respectively, of water, and the weak band at 2120 $cm^{-1}$ is due to a water combination vibration. The 3300 $cm^{-1}$ and 1636 $cm^{-1}$ bands also include contributions from the N—H stretching and amide I vibrations. The relatively flat absorption between 1500 and 900 $cm^{-1}$ and the rising absorption below 900 $cm^{-1}$ is also due primarily to water; however, in the intima, a number of very weak bands due to other tissue components are also present in this region.

Figure 9:
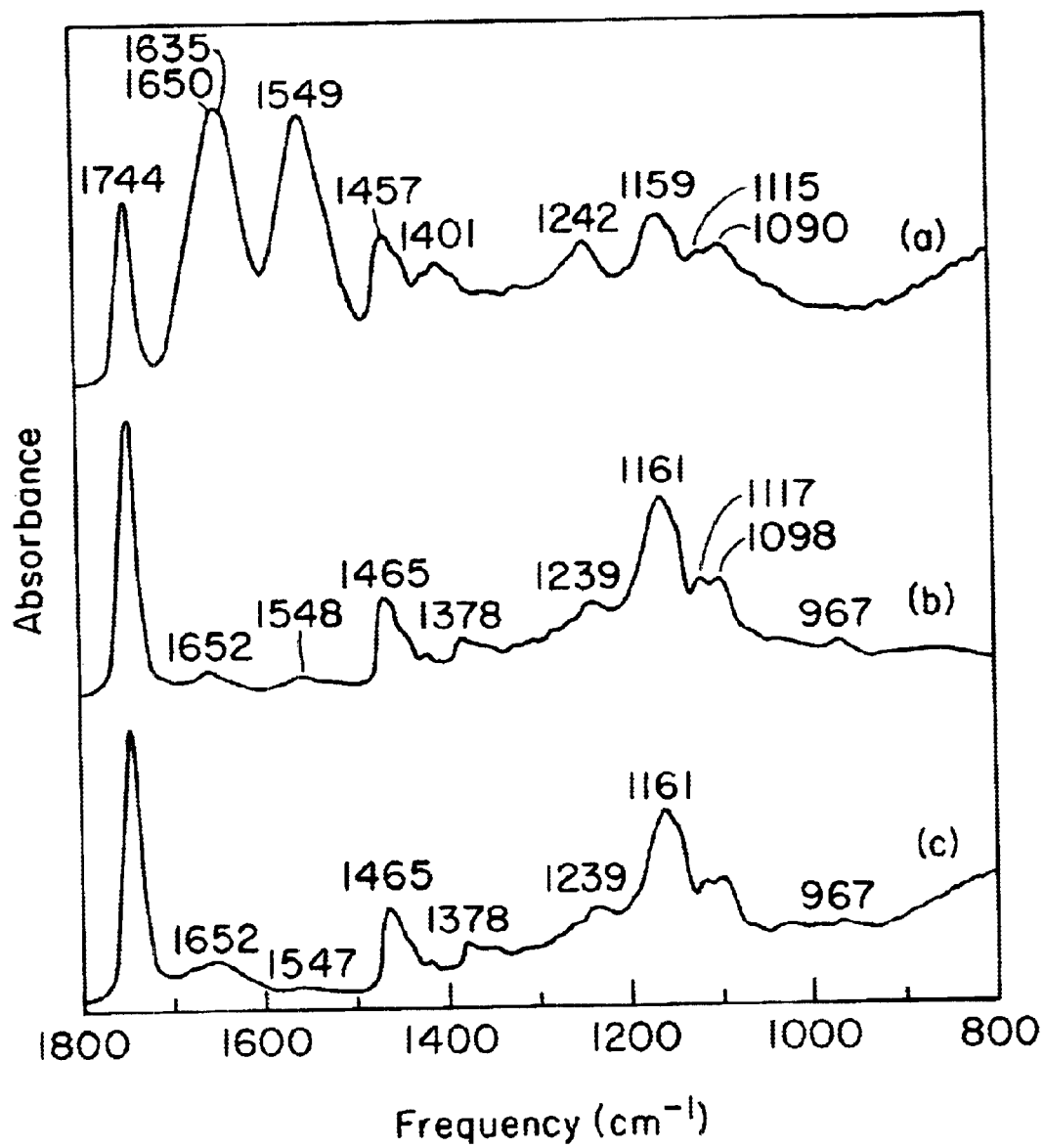
FIG. 9 graphically illustrates FT-IR ATR spectra (1800–800 $cm^{-1}$) after water subtraction: (a) Normal aorta, intimal surface; (b) Sub-adventitial fat; (c) Saline rinsed from the intimal surface of normal aorta.

Most biomolecules give rise to IR absorption bands between 1800 and 700 $cm^{-1}$, which is known as the "fingerprint region" or primary absorption region. The dominant absorption of tissue water in this region obscures the absorption bands from other tissue components. To observe the IR bands from these components, one must eliminate the water interference. With the ATR method, spectral deconvolution or subtraction of the water component is particularly easy. By using the 2120 $cm^{-1}$ band, which is due solely to water, as an internal intensity standard the spectrum of buffered saline (FIG. 8, curve b,) can be accurately and reliably subtracted from the spectrum of aorta intima (FIG. 8, curve a,), yielding a water-subtracted spectrum of intima (FIG. 9, curve a,).

In the water-subtracted spectrum, the previously weak bands are easily observed. Band assignments, based on the spectra of the major tissue components are listed in Table I. Most of the vibrational bands observed in the spectrum of normal intima (FIG. 9a) can be divided into two broad categories: lipid-associated bands and protein-associated bands. All of the strong bands in normal intima are associated with one of these moieties (see Table I). This can be seen as a simple consequence of the large concentrations of these two materials. Aside from water, a large fraction of tissue can be divided into one of these two groups. Moreover, both protein and lipid components contain repeating molecular units which are common to all members of the group. For

TABLE I

Preliminary assignments of IR absorption peaks in the ATR spectra of normal aorta intima.

| V (+1 $cm^{-1}$) | Preliminary Vibrational Assignment | Associated Tissue Components |
|---|---|---|
| 2923(s) | C—H stretch | Lipid, Protein, Others |
| 2853(s) | C—H stretch | Lipid, Protein, Others |
| 1744(s) | C=O (ester) stretch | Lipid |
| 1651(s) | Amide I | Protein |
| 1635(sh) | Amide I, H—O—H bend | Protein, Water |
| 1548(s) | Amide II | Protein |
| 1465(s) | $CH_2$ bend | Lipid |

TABLE I-continued

Preliminary assignments of IR absorption peaks in the ATR spectra of normal aorta intima.

| V (+1 cm$^{-1}$) | Preliminary Vibrational Assignment | Associated Tissue Components |
|---|---|---|
| 1457(s) | CH$_2$ bend, CH$_3$ anti-symmetric deformation | Lipid |
| 1454(m) | CH bend, CH$_3$ anti-symmetric deformation | Protein, others |
| 1417(w) | CH$_2$ bend adjacent to C=O | Lipid |
| 1401(m) | COO$^-$ symmetric stretch, amide C—N stretch | Protein, others |
| 1378(w) | CH$_3$ symmetric deformation | Lipid |
| 1244(m) | Amide III, PO$_2^-$ anti-symmetric stretch | Protein, others |
| 1239(m) | CH$_2$ wag, PO$_2^-$ anti-symmetric stretch | Lipid |
| 1159(s) | CH$_2$ wag, C—O—C antisymmetric stretch | Lipid |
| 1117(w) | C—C stretch, O—C—O stretch | Lipid |
| 1096 (w) | | Lipid |
| 1083(w) | PO$_2^-$ symmetric stretch | Protein, others |
| 1030(w) | | Lipid |
| 965(w) | C=CH deformation (trans) | Lipid |
| 722(m) | CH$_2$ rock | Lipid |

TABLE II

Peak frequencies of selected bands in normal and atheroscleriotic aorta.

| Normal | Adventitia[a] | Fibrous Plaque | Fatty Plaque | Exposed Calcif. I | Exposed Calcif. II | Assignments |
|---|---|---|---|---|---|---|
| | 1746w | | | | | C=O (ester) stretch |
| | | 1667m | 1667m | | 1667m | C=C Stretch Lipid |
| 1658s | | | | | | Amide I (8) |
| | 1655m | | | | | |
| | | | 1663m | | | C=C stretch Fatty Acids |
| | | | 1519w | | | Carotenoid (12) |
| 1451s | | | | 1450s | | C—H bend (8) |
| | 1440s | 1440s | 1440s | | 1440s | Protein Lipid |
| | 1301m | 1301w | 1301w | | 1300w | Lipid C—H bend (CH$_2$) |
| | | 1267w | 1264w | 1262w | | 1262w | Lipid C—H bend (=C—H) |
| 1252m | | | 1261w | | | Amide III (8) |
| | | 1157w | | | | Carotenoid (12) |
| | | 1131w | 1130w | 1128w | | C—C stretch Lipid |
| | 1080m | 1086w | 1088w | | | |
| | | | | 1071s | 1071s | Phosphate antisymmetric stretch Calcium salts (15) |
| 1004w | | 1004w | 1004w | | | Phenylalanine (8) |
| | | | | 960vs | 960vs | Phosphate symmetri stretch Calcium salts (15) |
| | | 957w | 956w | | | Cholestreols (11) |
| | | 882w | 882w | 878w | | |
| | | 842w | 841w | 850w | | |
| | | 803w | 801w | 804w | | |
| | | 700m | 700m | | 699m | |
| | | 606w | 606w | | | |
| | | 546w | 546w | | 547w | |
| | | | | 587m | 587m | Phosphate Calcium salts (15) |

Peak frequencies of typical specimens, accurate to ±1 cm$^{-1}$.
Abbreviations: vs = very strong, s = strong, m = medium, and w = weak relative band intensity.
[a]Adventitia specimen is mainly adipose tissue.

protein, the polypeptide backbone of repeating amide groups is the dominant element. In lipids, the repeating hydrocarbon chain is the defining quality. The end result is that these molecular units are present in very large concentrations, and their vibrational bands tend to dominate the spectrum. Note that this does not imply that no further level of detail is derivable from the IR spectrum of tissue. For example, the frequencies of the amide group vibrations are sensitive to protein configuration and conformation. Therefore, shifts in protein makeup might be expected to produce observable changes in the amide bands.

The water-subtracted spectrum of sub-adventitial fat shown in FIG. 9, curve b, more clearly illustrates the division of bands into lipid and non-lipid categories. This fat can be considered as the model of the lipid component. Protein contributions, as judged from the intensities of the amide I and II bands, are negligible for the purposes of this model. All of the bands observed in the fat spectrum can be attributed to the lipid component. These include the strong bands at 1744 cm$^{-1}$ (C=O stretch), 1465 cm$^{-1}$ (C—H bend), 1161 cm$^{-1}$ (CH$_2$ wag, C—O—C stretch), as well as the weaker bands at 1378 cm$^{-1}$, 1239 cm$^{-1}$, 1118 cm$^{-1}$, 1099 cm$^{-1}$, 966 cm$^{-1}$, and 722 cm$^{-1}$.

Figure 10:
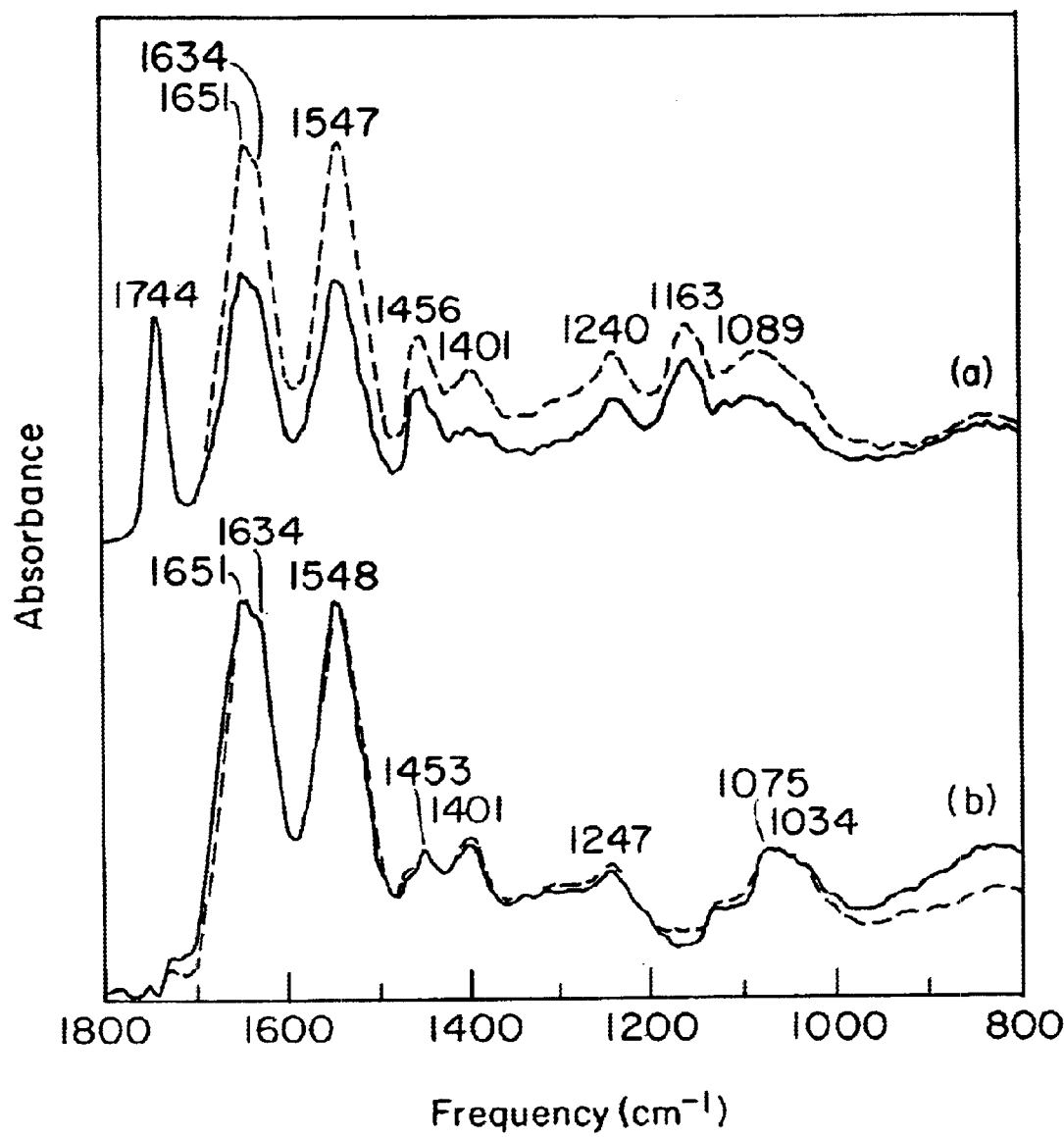
FIG. 10 graphically illustrates FT-IR ATR spectra (1800–800 $cm^{-1}$): (a) Two consecutive water-subtracted spectra of normal aorta, intimal surface, collected immediately after placement on ATR element (solid line) and 10 minutes later (dashed line); (b) Same two spectra as in (a) after lipid subtraction, scaled to have equal maxima.

The bands observed in the water-subtracted spectrum of intima constitute less than 30% of the total absorption, the rest being due to water. Any conclusions regarding these relatively weak bands depends critically upon the accuracy of the water substraction. The accuracy of this subtraction can be judged from the reproducibility of spectra obtained sequentially from the same sample. Two consecutive water-subtracted spectra collected 10 minutes apart from a sample of normal aorta (intimal side) are shown in FIG. 10, curve a, (solid and dashed curves). Most of the IR bands exhibit a substantial increase in absorbance with time. This trend continues for consecutive spectra collected more than an hour after the placement of the sample on the ATR element. However, not all of the bands change by the same fraction, so that the relative intensities differ between consecutive spectra. For instance, in FIG. 10, curve a, the C=O band at 1744 cm$^{-1}$ is relatively constant, while the amide bands at 1650 cm$^{-1}$ and 1547 cm$^{-1}$ increase by 50% in the later spectrum. Although these changes might seem to indicate that the water subtraction is inaccurate, the changes with time are systematic and predictable, which suggests that the optical contact between the sample and the ATR element is changing regularly with time.

In fact, the constancy of the 1744 cm$^{-1}$ C=O band, which is due solely to lipid, and the increases in the amide bands, which are due to protein, indicate that the lipid contributions to the IR absorption remain unchanged while the non-lipid contributions increase between consecutive scans. This is confirmed by subtracting the spectrum of lipid (FIG. 9b) from the water-subtracted spectra of aorta intima (FIG. 10, curve a,), using the 1744 cm$^{-1}$ band for normalization. The resulting lipid-subtracted spectra of aorta intima are shown, normalized to peak absorbance, in FIG. 10b. As can be seen, the relative peak absorbencies and spectral bandshapes in the lipid-subtracted spectra reproduce quite well, reflecting the accuracy of both the water and the lipid-subtraction procedures.

The constancy of the lipid bands and the variation of the non-lipid bands between successive scans may seem somewhat puzzling. An explanation of this apparent anomaly can be inferred from a water-subtracted spectrum of saline solution which is rinsed off the surface of the tissue (FIG. 9c). This spectrum, aside from the weak amide I and II bands, matches quite closely with that of adventitial fat. The lipid component observed in the tissue appears to be due to free lipid particles that have equilibrated with the tissue surface water, forming a thin water-lipid film on the tissue surface which is in full optical contact with the ATR element immediately after the tissue specimen is placed upon the crystal. The tissue components beneath this film presumably achieve better optical contact with the ATR crystal as the sample settles. As a result, the content of lipid in a spectrum of aorta intima or media may be influenced by the presence of sub-adventitial fat in the specimen, and the relative lipid-protein absorbencies are accurate to 50% at best with the present experimental design. For the reason, all of the remaining spectra shown are both water and lipid subtracted.

With the lipid bands removed, assessment of the non-lipid bands in the spectrum of normal intima (FIG. 10b) is greatly simplified. The major bands in the spectrum may be assigned to protein backbone vibrations. These include the bands at 1648 cm$^{-1}$ (amide I), 1549 cm$^{-1}$ (amide II), 1455 cm$^{-1}$ (C—H bend), 1401 cm$^{-1}$ (amide C—N stretch), and 1244 cm$^{-1}$ (amide III). The frequency of the amide I peak (1648 cm$^{-1}$), which is sensitive to protein secondary structure, may indicate contributions from α-helix, disordered, and collagen helix conformations. This band also exhibits a shoulder near 1634 cm$^{-1}$, which may be due to the β-sheet regions of proteins or water. The protein C—H bending band at 1455 cm$^{-1}$ is distinct from the corresponding vibration in lipid, which occurs as a double-peaked band at 1465/1457 cm$^{-1}$. Note that all of these bands may include contributions from other moieties. For instance, the symmetric stretch of carboxylate groups and the antisymmetric stretch of phosphate groups may also contribute, respectively, to the 1401 cm$^{-1}$ and 1244 cm$^{-1}$ bands. This correlation of components is summarized in Table I above.

Figure 11:
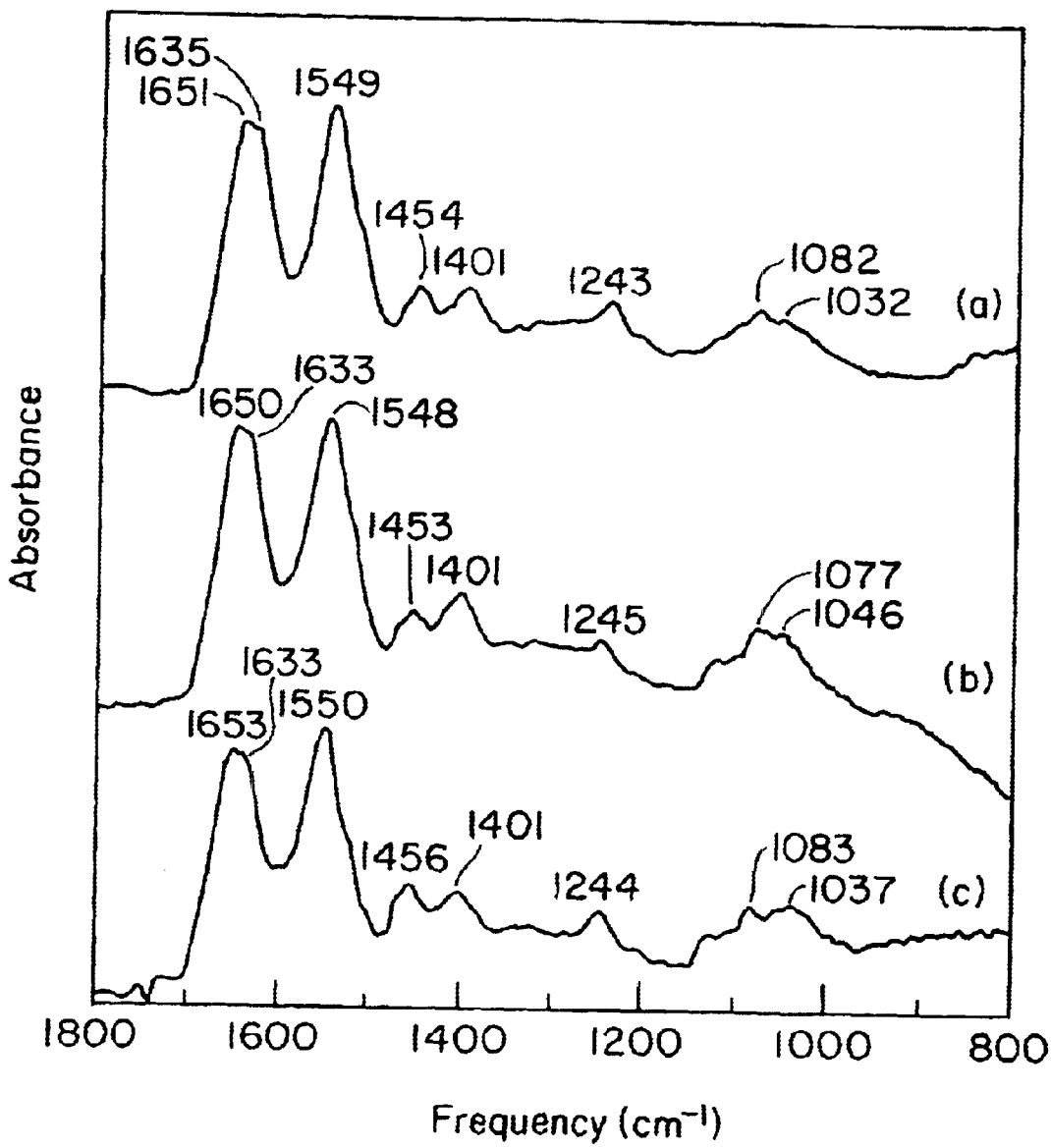
FIG. 11 graphically illustrates FT-IR ATR spectra (1800–800 $cm^{-1}$), water-and lipid-subtracted: (a) Normal aorta, media layer; (b) Atherosclerotic plaque, intimal surface; (c) Atheromatous plaque with intact fibrous cap, intimal surface.

A typical spectrum of the medial layer of normal aorta is shown in FIG. 11a. A comparison of this spectrum to that of normal intima (FIG. 10b) fails to reveal any significant differences. This result is somewhat surprising, considering that normal aorta intima and media have significantly different compositions. Typical spectra of an atherosclerotic plaque and a non-ulcerated atheromatous plaque are shown in FIGS. 11b and 11c, respectively. For these plaques, only the intact fibrous cap at the intimal surface is probed due to the short penetration depth (1 μm) of the beam. Any necrotic, atheromatous material beneath this fibrous cap is not sampled. Even so, the fibrous caps of these plaques are known to be compositionally different than normal intima and one might expect these differences to be reflected in the IR ATR spectrum. However, as in the case of media, no consistent differences are observed in the spectra of these plaques (FIGS. 11b and 11c) and normal intima (FIG. 10b). This issue will expanded upon in the discussion below.

On the other hand, substantial differences are obvious in the spectrum of the necrotic, atheromatous core of an atheromatous plaque (FIG. 12a) as compared with the corresponding spectra of normal intima (FIG. 10b) as well as those of intact atherosclerotic (FIG. 11b) and atheromatous (FIG. 11c) plaques. In this case, the necrotic core was presumably exposed in vivo as disease progressed by ulceration of the overlying intimal fibrous tissue cap. (The spectrum of necrotic core exposed by dissecting away the fibrous cap of a non-ulcerated atheromatous plaque is similar.) A new band appears at 1050 cm$^{-1}$, with a secondary peak at 1023 cm$^{-1}$. In addition, the necrotic core spectrum exhibits an increase and frequency shift in the 1466 cm$^{-1}$ band as compared with the 1455 cm$^{-1}$ protein band in normal intima as well as a set of unique bands near 1382 cm$^{-1}$. These characteristic bands are found in the spectra of all the exposed necrotic core samples and in none of the other samples (see below).

The source of these unique bands in the necrotic core spectra may be cholesterol, which is known to accumulate in large amounts in atheromatous cores. An ATR spectrum of cholesterol (dry film) is shown in FIG. 12b. The three major bands unique to the necrotic core, near 1463 cm$^{-1}$, 1382 cm$^{-1}$, and 1050 cm$^{-1}$, match closely in position and relative intensities with the three main cholesterol bands at 1466 cm$^{-1}$, 1377 cm$^{-1}$, and 1056 cm$^{-1}$. Each of the main cholesterol bands has a secondary peak, which also appear to be present in the necrotic core bands. These secondary peaks occur at 1445/1436 cm$^{-1}$, and 1023 cm$^{-1}$ in the cholesterol spectrum and at 1441 cm$^{-1}$, 1367 cm$^{-1}$, and 1023 cm$^{-1}$ in the necrotic core spectrum. In addition, several of the weak bands in the necrotic core spectrum, including the peaks at 1334 cm$^{-1}$, 1109 cm$^{-1}$, 954 cm$^{-1}$, and 797 cm$^{-1}$, are associated with the weaker cholesterol bands near these frequencies. Other components in the necrotic core may also contribute to some of these distinct bands.

Figure 13:
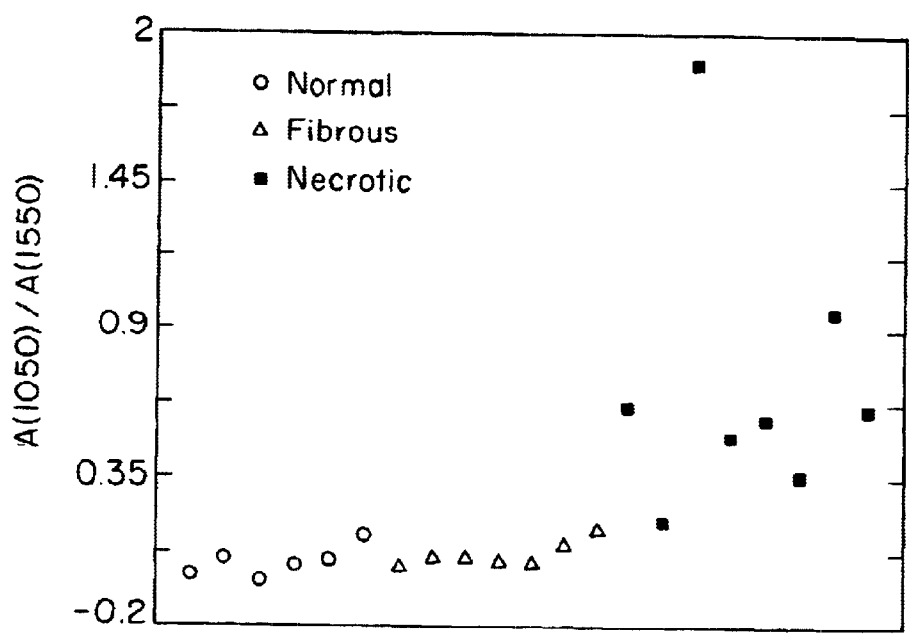
FIG. 13 graphically illustrates scatter plot for all samples of the area, A(1050), of the 1050 $cm^{-1}$ cholesterol band (integrated from 1075 to 1000 $cm^{-1}$) ratioed to the area, A(1550) of the 1548 $cm^{-1}$ protein amide II band (integrated from 1593 to 1485 $cm^{-1}$). The intensities were calculated from the water-and lipid-subtracted spectra. NORMAL denotes normal aorta specimens, intimal side, FIBROUS includes atherosclerotic and atheromatous plaques with intact fibrous caps, and NECROTIC includes exposed necrotic atheroma cores and necrotic material isolated from atheromatous plaques.

The consistency of the spectral differences which are attributed to cholesterol between the necrotic core specimens and the normal, atherosclerotic, and non-ulcerated atheromatous specimens are illustrated in the scatter plot in FIG. 13. This plot depicts the integrated intensities (areas) of the 1050 cm$^{-1}$ cholesterol band ratioed to the total protein content, as measured by the area of the amide II band at 1548 cm$^{-1}$. The 1050 cm$^{-1}$ band was integrated from 1075 to 1000 cm$^{-1}$ and baseline subtracted using these endpoints, and the amide II band was integrated from 1593 to 1485 cm$^{-1}$ with a similar baseline subtraction. This ratio is a measure as the relative cholesterol contribution to the spectrum, and is proportional to the relative cholesterol concentration of the sample with the assumption that the area of the 1050 cm$^{-1}$ band is due solely to cholesterol. As can be seen in FIG. 13, this ratio is higher for all the exposed necrotic core specimens than for all the other specimens. The consistent results of this sample analysis, which is possible because of the separation and molecular identification of the bands, indicates the potential of IR spectroscopy for tissue characterization.

Investigations of human arteries and atherosclerosis by mid-IR spectroscopy have been limited to date. It has been reported that ATR spectra have been recorded from partially dried human artery, among other tissues. In comparing a normal aorta from an infant to an atherosclerotic plaque in an adult, they observed increases in several bands in the atherosclerotic aorta. Most of these bands were associated with lipids and lipoproteins. IR spectroscopy has been employed to determine the chemical composition of calcified atherosclerotic deposits. A more detailed IR study of atherosclerotic aorta involves recorded IR transmission spectra from thin layers sectioned at different depths into the arterial wall. Results showed increased absorption near 1739 $cm^{-1}$ in the fatty (atheromatous) regions of plaque, which was attributed to absorption by cholesterol esters in the plaque. IR spectra from the fibrous tissue cap at the surface of the plaques were similar to normal intima.

One of the main difficulties in measuring mid-infrared spectra of intact human tissue is the intense water absorption, which dominates and obscures the absorption of other tissue components of interest. In most of the studies cited above, the water absorption was not eliminated, limiting the quality and amount of information available from the spectra. With the ATR sampling method, this water interference is easily removed (see FIG. 9). The ATR method is also naturally amenable to sampling with fiber optic probes in vivo. Water interference in fiber optic probe ATR spectra of aqueous protein solutions has been accurately eliminated with a water subtraction procedure similar to the one employed in the present study.

While the ATR method is well suited to in vivo sampling and to accurate subtraction of the water signal, spectra collected with the ATR method are not equivalent to IR absorption spectra, but depend on properties of the ATR material and the sample in addition to the sample absorption coefficient. For instance, the penetration depth of the evanescent sampling wave depends on the refractive indices of the ATR material and the sample. However, the refractive indices of both ZnSe and human tissue are expected to vary slowly with frequency between 1800 and 700 $cm^{-1}$ and such variations will at most affect the relative intensities of bands at different frequencies. All of the structure observed in the tissue spectra is attributed to absorption bands in the tissue.

The component absorptions observed in an ATR spectrum also depends upon the optical contact of the sample and ATR element. The small penetration depth of the evanescent wave into the tissue sample implies that only a 5 $\mu$m thick layer, and preferably about 1 micron, of material at the surface is observed. This is referred to as the near surface region of the tissue for the purposes of this application. The tissue deeper than 5 microns from the surface is defined as the sub-surface region. This thin, sampled near-surface layer may differ in composition with the bulk sample. For example, a film of free water may be present on the surface of wet tissue, with different levels of some molecular species of the tissue relative to their concentrations in the bulk tissue. In addition, the varied affinities for the ATR material of different moieties in the tissue may play an important role in the intensities of the observed bands.

These considerations may explain the lack of substantial differences among the ATR spectra of normal intima, plaque fibrous cap, and media. For instance, normal aorta intima is composed of roughly 25% collagen (dry weight) and 20% elastin, while aorta media has 20% collagen and 50% elastin. The ATR spectra of purified collagen and purified elastin (not shown) differ substantially. In particular, amide I/II occur at 1657/1556 $cm^{-1}$ in hydrated collagen (type I) and 1653/1543 $cm^{-1}$ in hydrated elastin (spectra not shown).

One might expect these differences to be reflected in the intima and media ATR spectra. A possible explanation of why this is not the case is that the thin layer in optical contact wit the ATR element is compositionally different from the bulk tissue, and collagen and elastin make only a minor contribution to the IR ATR bands of this layer. Such an effect may also explain the lack of significant differences among the plaque fibrous cap intima and normal intima ATR spectra. In ATR elements made of other substances with different biochemical affinities, the spectral differences among these tissues can be substantially enhanced depending on the tissue type.

The results of the present investigation demonstrate that high quality water-subtracted spectra can be readily obtained from human tissue with the ATR technique. Similar results have been obtained in other mammalian tissues. Accurate removal of the water interference is crucial to isolating the relatively weak tissue absorption bands of lipid, protein, as well as other tissue components. It is worth noting that the observation of these relatively weak bands via spectral subtraction depends entirely upon quality of the tissue and saline spectra. For instance, the absorbance of the normal intima specimen (FIG. 8a) between 1500 and 900 $cm^{-1}$ is approximately 0.06. In the water-subtracted spectrum (FIG. 9a), the peak absorbencies range from 0.018 (30%) for the strongest bands to 0.003 (5%) for the weakest ones. The detection of a 0.003 absorbance peak in a subtracted spectrum with a 0.06 absorbance background requires a signal-to-noise ratio of 700 or better in the 100% baseline. Such a signal-to-noise is easily achieved with an FT-spectrometer. The high linearity, baseline stability, and wavelength precision of the FT-spectrometer are also obviously critical for accurate background subtraction.

While water subtraction is relatively easy and accurate with ATR, it may be substantially more difficult with other clinically applicable sampling techniques such as diffuse reflectance or photoacoustic sampling. These alternative sampling techniques are clinically useful, however, because of their longer tissue penetration depths (approximately 10 $\mu$m). As an alternative to water subtraction, one can exploit the properties of the spectral lineshape of water to eliminate the water signal by other computational methods. Specifically, the spectral lineshape of water varies rather slowly with frequency over much of the region of interest, especially between 1500 and 700 $cm^{-1}$. Therefore, any method which filters this slower variation and spares the sharper features of the non-water bands can separate the water and non-water components.

Figure 14:
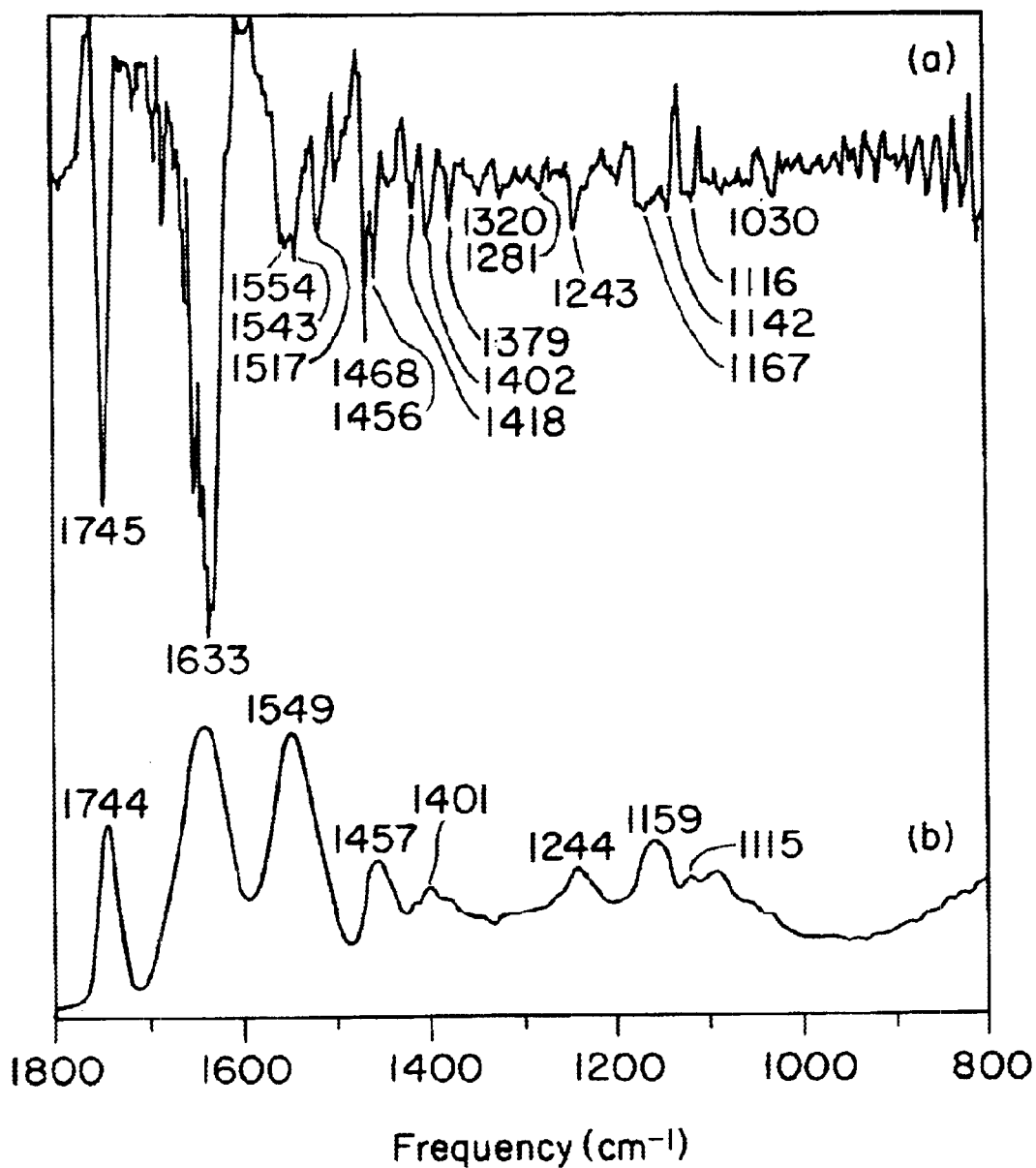
FIG. 14 graphically illustrates FT-IR ATR spectra (1800–800 $cm^{-1}$): (a) Second derivative spectrum of normal aorta intima (FIG. 8a); (b) Water-subtracted spectrum of same normal aorta intima specimen (same as FIG. 9a).

One such method is second derivative spectroscopy. Differentiation of a spectrum is typically used to narrow absorption bands and resolve overlapping peaks. Differentiation also tends to deemphasize broad bands relative to sharper ones. In IR spectra of artery, the broad, featureless absorption of water can be nearly eliminated in favor of the sharper non-water bands by computing the second derivative of the spectra. This is clearly demonstrated in FIG. 14, which shows the second derivative of a spectrum of normal aorta intima (FIG. 14a), along with the water-subtracted spectrum of the same specimen (FIG. 14b). Essentially only the 1633 $cm^{-1}$ water band is left, partially obscuring the amide I band. Elsewhere in this spectrum, the water contribution is minimal. All of the bands identified in the water-subtracted spectrum are easily observed in the second derivative spectrum.

In addition to elimination of water interference, several of the unresolved double peaks and shoulders in the water-subtracted spectrum appear as distinct peaks in the second derivative spectrum. For example, the amide II band in normal intima (FIG. 14b) has a very weak shoulder near 1518 $cm^{-1}$, and the C—H bending region near 1468 $cm^{-1}$ appears to include two overlapping peaks. In the second derivative spectrum (FIG. 14a), the 1518 $cm^{-1}$ band is clearly visible, and the C—H region exhibits two separate peaks at 1469 and 1456 $cm^{-1}$. Moreover, by sharpening the bands, the second derivative spectrum allows a more precise determination of peak frequencies, so that relatively small frequency shifts are observed. Such frequency shifts can be of importance in detecting and characterizing subtle molecular alterations involved in certain tissue conditions.

The observation of individual, resolved bands in the artery IR ATR spectra is of considerable interest, since separation of bands is the first step determining the composition of a sample from its spectrum. Once a band has been isolated, its integrated intensity is proportional to the concentration of the moiety responsible for that band. In particular, since the amide I and II bands are due entirely to protein, these bands can be used to isolate the overall protein content in the spectrum. The sharp, well resolved 1744 cm$^{-1}$ C=O ester band appears to be due to solely to lipid, and the integrated intensity of this band should be proportional to the relative lipid content are technique should largely eliminate the inaccuracies. Finally, it should be remembered that the relative water content of the tissue sample is automatically computed from the 2120 cm$^{-1}$ band in the water subtraction algorithm. However, as noted earlier, the composition of tissue as determined from an ATR spectrum may not be precisely identical to the composition of the bulk tissue.

The tissue composition can also be determined from overlapping bands by first deconvolving the bands of interest into their individual components. This is especially easy if one component has an additional, isolated band elsewhere in the spectrum. An example is the 1465 cm$^{-1}$ C—H bending region, which is due to different tissue components with distinct spectral features in this region. In the normal intima spectrum (FIG. 9a), this band is attributed to a combination of lipid and protein components. Since the lipid component also exhibits the isolated 1744 cm$^{-1}$ band, this band can be used to subtract the lipid C—H bending component and isolate the protein C—H bending component at 1455 cm$^{-1}$ (FIG. 10b), effectively deconvolving this band. Note that this deconvolution depends on having a reliable spectrum of one of the individual components, which, in this example, is the lipid spectrum in FIG. 9b.

Figure 12:
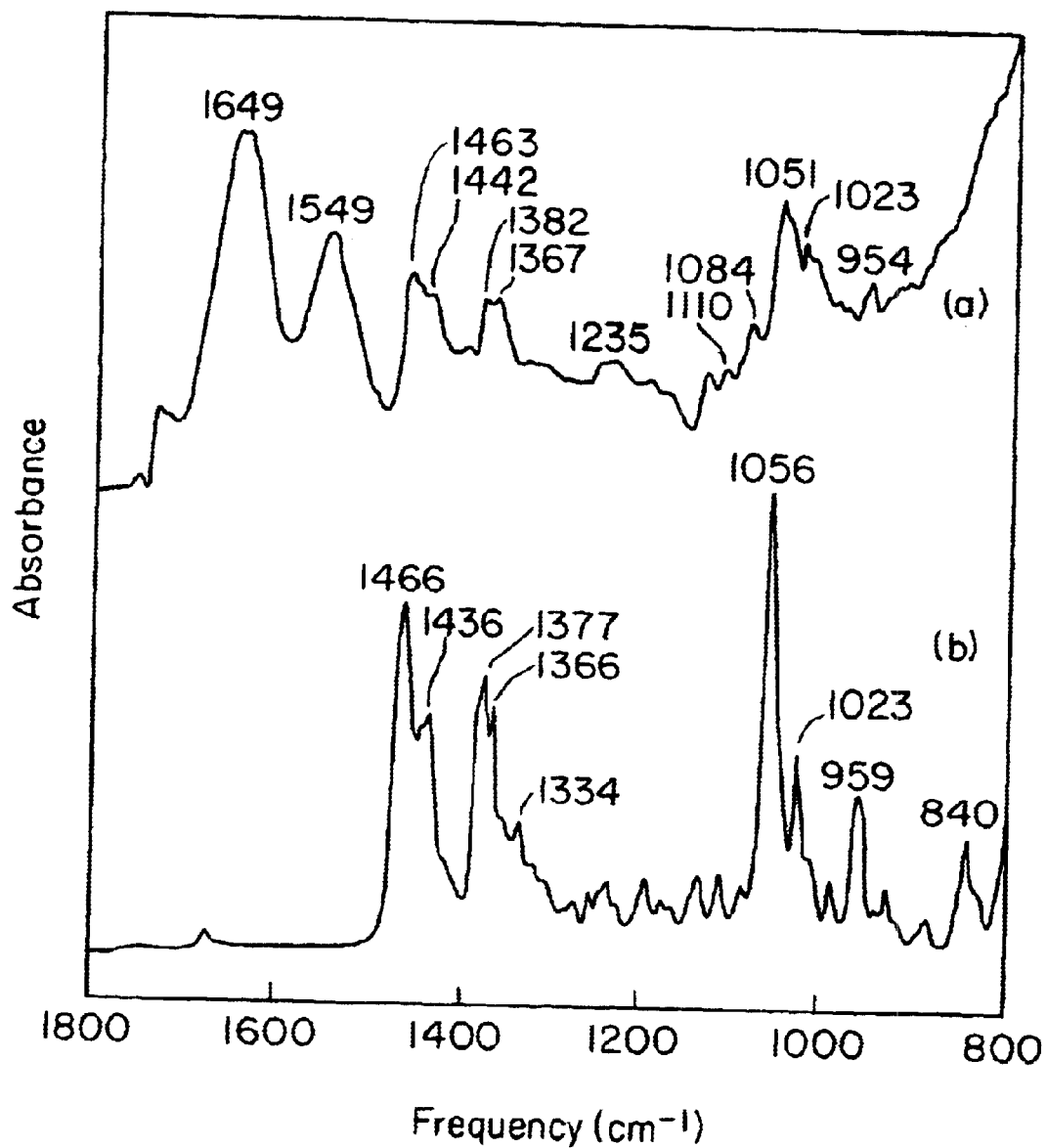
FIG. 12 graphically illustrates FT-IR ATR spectra (1800–800 $cm^{-1}$): (a) Necrotic core of atheromatous plaque, water-and lipid-subtracted; (b) Dry film of cholesterol.
Figure 15:
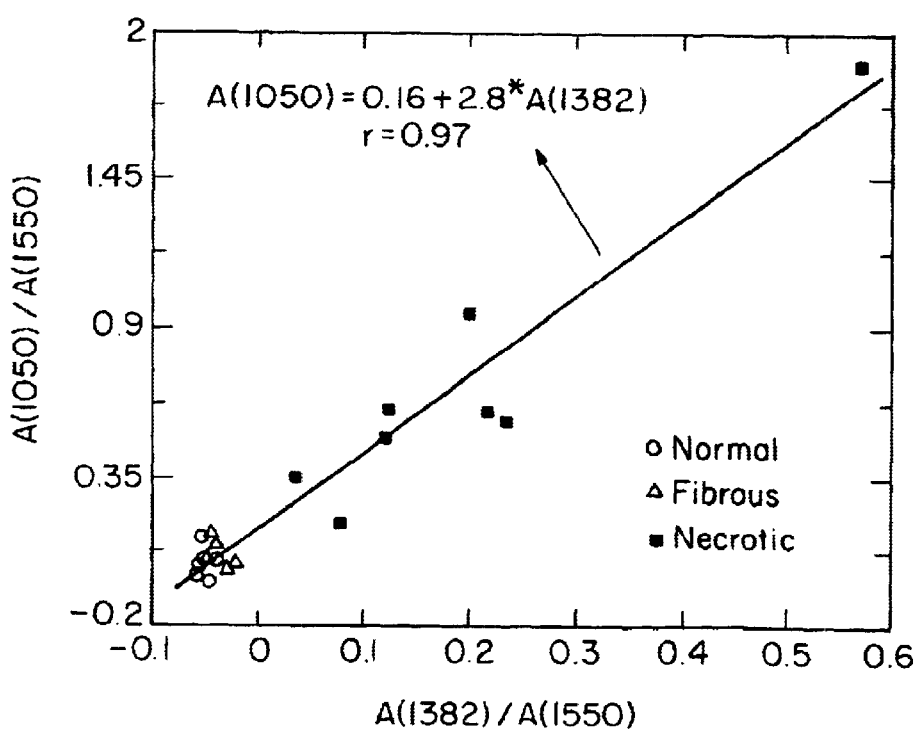
FIG. 15 graphically illustrates a scatter diagram for all the specimens of the area, A(1050) of the 1050 $cm^{-1}$ cholesterol band plotted versus the area, A(1382), of the 1382 $cm^{-1}$ cholesterol band. Both cholesterol bands have been normalized to the area, A(1050), of the protein amide II band. All band intensities were calculated from the water-and lipid-subtracted spectra. Tissue categories are the same as in FIG. 13. The solid line represents a linear least squares fit to the data.

The detection of distinct bands attributed to cholesterol in necrotic core may provide a useful means of determining cholesterol concentrations in vivo. Both the 1050 cm$^{-1}$ and 1382 cm$^{-1}$ cholesterol bands appear to be fairly isolated in the necrotic core spectrum after lipid-subtraction (FIG. 12). If these two bands are due to a single component, namely cholesterol, the ratio of their integrated intensities should be a constant for all the samples. The baseline-subtracted area of the 1050 cm$^{-1}$ band, A(1050), is plotted versus that of the 1382 cm$^{-1}$ band, A(1382), for all the samples, normalized to the protein content in FIG. 15. As can be seen in the plot, there is a roughly linear relationship between A(1050) and A(1382). A linear least squares fit to this data yields the line shown in the plot, with a high regression coefficient of r=0.967. The slope of this line 2.8, while the ratio A(1050)/A(1382) for the pure cholesterol ATR spectrum is 2.3. The reasonable agreement between these two numbers provides additional evidence for the assignment of these bands to cholesterol. Moreover, it indicates that the relative spectral content of cholesterol is reasonably approximated by the integrated intensities of either of these bands. FIG. 15 also shows that the ATR spectra of all the specimens other than exposed necrotic core exhibit almost no intensity in both the 1050 and 1382 cm$^{-1}$ bands, in contrast to the necrotic specimens, all of which have significant bands at both frequencies.

The present systems and methods demonstrate that infrared spectra of moist, bulk tissues can be reliably obtained with the ATR technique. Although water is the dominant absorber throughout much of the mid-infrared region, the high quality spectra acquired with the FT-IR ATR technique allow for accurate subtraction of the water signal. Elimination of the water interference is critical for identifying and assigning the absorption bands of other tissue species. The isolation and designation of these relatively sharp bands provides a means of analyzing spectroscopically the composition of arterial tissue non-destructively. There methods are also applicable to the study and diagnosis of other tissues and tissue conditions, such as neoplasia.

The observation of both lipids and cholesterol in the spectra of necrotic atheromatous core samples is particularly exciting, because lipids and cholesterol are thought to play major roles in the pathogenesis of atherosclerosis. The spectral observation of these components, cholesterol in particular, provides a reliable means of detecting and characterizing advanced atheromatous plaques in which ulceration of the fibrous cap has occurred (as demonstrated in FIGS. 13 and 15). Intimal accumulations of lipid and cholesterol occur early in the atherogenic process. Therefore, the mid-IR ATR technique can also be useful in detecting and studying the early fatty streak lesion.

Spectrograph/CCD System for NIR Raman Spectra

NIR Raman spectroscopy using a single stage spectrograph and a charge coupled device (CCD) detector offers superior sensitivity over the Nd:YAG excited FT-Raman system of FIGS. 1A and 1C. By shifting the wavelength of the laser excitation from 1064 nm to the 800–900 nm region, a CCD can be used to detect the Raman scattered signals while still avoiding fluorescence excitation in most molecules. The system can operate usefully in the range of 750 nm to 1050 nm. Although the fluorescence emission from tissue is significantly higher with 810 nm than with 1064 nm excitation, the Raman signals are readily observed. This is because the dominant noise source in the spectrograph/CCD system is shot noise associated with the fluorescence emission, which is 2–3 orders of magnitude smaller than the dark current noise of the InGaAs detector, which is the dominant noise source in the FT-Raman system.

Figure 17:
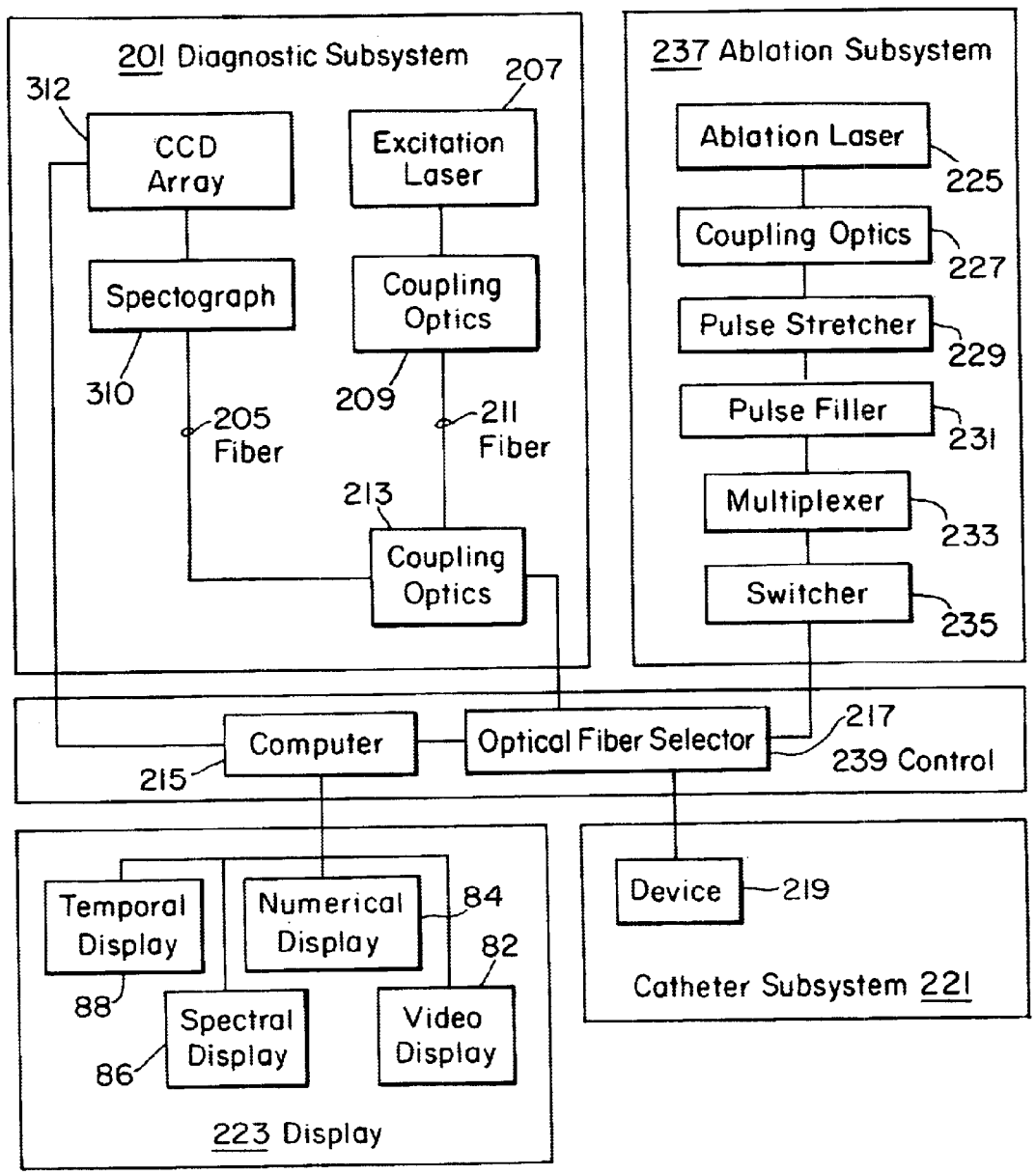
FIG. 17 is a schematic diagram of the system of FIG. 1A modified to use the spectrograph/CCD Raman detector of the present invention.

FIG. 17 shows the laser diagnosis and treatment system of FIG. 1A modified to use the spectrograph/CCD system of this invention. The diagnostic subsystem 201 includes a single stage spectrograph 310 and charge-coupled device (CCD) detector 312 for collecting near-infrared (NIR) Raman spectra from intact human arterial tissue. With 810 nm laser light excitation, preferably pulsed, the fluorescence emission from human artery tissue is sufficiently weak to observe Raman bands more rapidly with the spectrograph/CCD system than with the 1064 nm excited FT-Raman system of FIGS. 1A and 1C. A method for removing the broadband emission from the spectra by computing the difference of two emission spectra collected at slightly different excitation frequencies was used to enhance observation of the Raman bands. This method relies on the stability, linearity, and low noise characteristics of the CCD detector. The results indicate that high quality NIR Raman spectra can be collected in under 1 second with the spectrograph/CCD system and an optical fiber probe, as compared to 30 minutes with the FT-Raman system at similar laser power levels, further improving the use of the technique for in vivo clinical applications.

Figure 18:
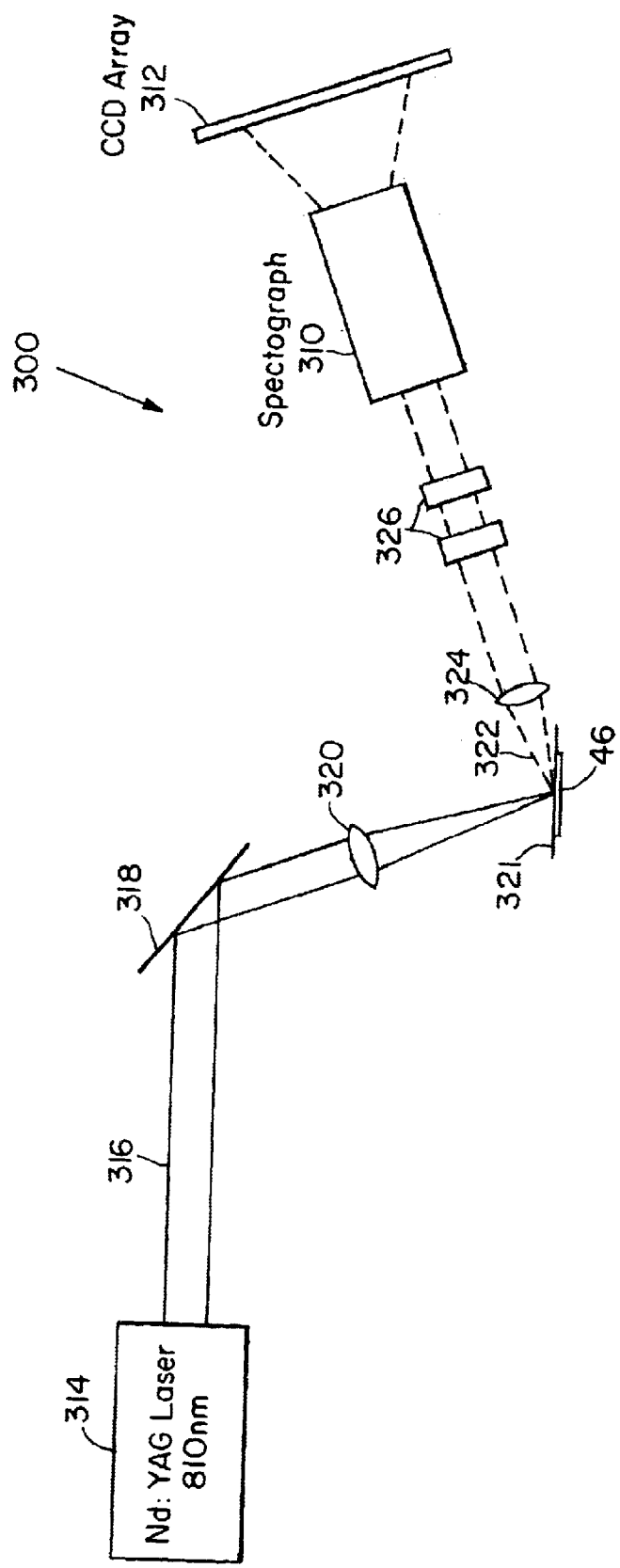
FIG. 18 is a schematic diagram of a preferred system for implementing the spectrograph/CCD Raman detector of the present invention.

A preferred embodiment of a spectrograph/CCD system 300 employed for the collection of near infrared (NIR) Raman spectral data from excised tissue samples using a spectrograph and a charge coupled device (CCD) array is illustrated in FIG. 18. NIR Raman spectra were measured from 100–2000 cm$^{-1}$ below the laser excitation frequency with a single stage imaging spectrograph 310 (Acton Model ARC275, 0.25 m, F/3.8) and a CCD array 312 (Princeton Instruments EEV Model 88130).

System 300 can use a NIR 810 nm Nd:YAG pumped pulsed dye laser 314 operating at 10 Hz for irradiating a sample 46. Alternatively, a CW or diode laser source can also be employed. Laser 314 generated a laser beam 316 which is directed by mirror 318 through focusing optics 320 to impinge on sample 46 mounted behind a transparent window 321. The laser beam was focused on the sample at a 70° angle of incidence, yielding a spot size of 0.7×2 mm on the tissue surface. The average incident power at the sample was maintained at 20 mW to avoid excessive peak intensities during an individual pulse. The spectral signals were observed to be linear over a range of average incident powers from 2 to 20 mW.

A portion of the scattered light 322 emitted by sample 46 was collected by collecting optics 324 at a 90° angle relative to the incident laser beam. Collecting optics 324 collimates and F/matches the collected light for the spectrograph 310. Prior to entering the entrance slit of the spectrograph 310, the collected light was passed through a series of Schott glass filters 326 which attenuated the elastically scattered component of the collected light. The combined effect of the Schott glass filters provided an optical density of 7 at 810 nm, a transmission of 20% at 850 nm (580 cm$^{-1}$ from 810 nm), and a transmission of 85% above 900 nm (1200 cm$^{-1}$).

The spectrograph 310 utilized a 200 μm slit width and a 600 groove/mm grating blazed at 1 μm and could be scanned to provide spectral coverage over different wavelength regions. The 200 μm slit width provided a resolution of roughly 15 cm$^{-1}$.

The CCD array 312 consisted of 298 (column) by 1152 (row) pixel elements having a total active area of 6.7 mm×26 mm, with the short axis parallel to the slit. The CCD array was cooled to −110° C. to eliminate dark current. Each row of pixels was binned to reduce readout noise. Commercially available CCD detectors offer extremely low detector noise and usable quantum efficiencies out to 1050 nm and provide substantial advantages over InGaAs and other NIR detectors. These advantages outweigh the lower throughput of the grating spectrograph, provided that broadband fluorescence interference is not too great with the shorter excitation wavelengths.

Excised human aorta samples 46 obtained at the time of post-mortem examination were rinsed with isotonic saline solution (buffered at pH 7.4), snap-frozen in liquid nitrogen, and stored at −85° C. Prior to spectroscopic examination, samples were passively warmed to room temperature and were kept moist with the saline solution. Normal and atherosclerotic areas of tissue were identified by gross inspection, separated, and sliced into roughly 8×8 mm pieces.

The tissue samples 46 were placed in a suprasil quartz cuvette with a small amount of isotonic saline to keep the specimens moist, and with one surface in contact with the transparent window 321 and irradiated by the laser 314.

Raman spectra were typically measured between 100 cm$^{-1}$ and 2000 cm$^{-1}$ below the laser excitation frequency. Each spectrum was background subtracted to remove the DC offset of the A/D converter of the CCD controller. In addition, hot pixels due to high energy radiation events were removed from the recorded spectrum by applying a median filter having a 7 pixel wide window as to each spectrum. Raman frequencies were calibrated with the spectra of benzene and barium sulfate powder and are accurate to ±5 cm$^{-1}$. The spectra were not corrected for the wavelength dependent response of the filters, spectrograph, and CCD. For each spectrum shown in the following Figures, Raman signals were accumulated for 5 minutes. Substantially shorter collection times can also be used as described herein.

Figure 19:
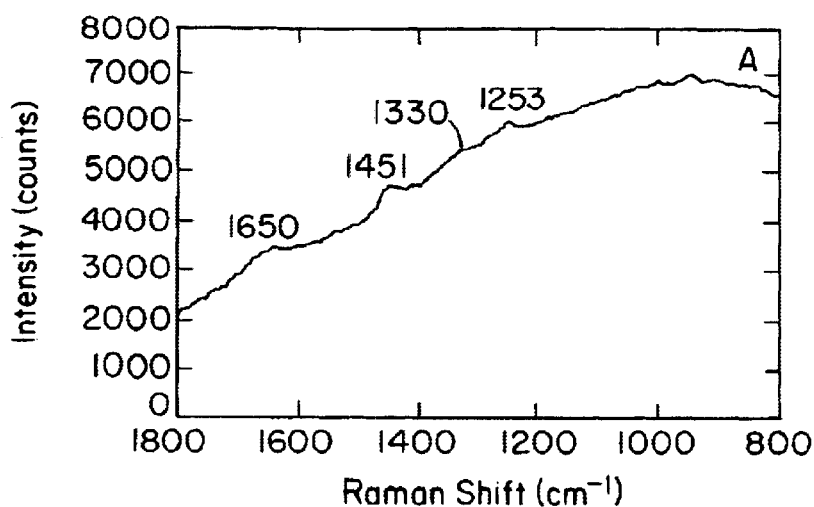
FIG. 19 graphically illustrates spectrograph/CCD-Raman spectra of normal human aorta: A) Raman plus fluorescence spectrum produced by illuminating the tissue sample with 810 nm laser light; B) Raman difference spectrum produced by subtracting spectra produced by illuminating the tissue sample with 810 and 812 nm laser light; C) resulting Raman spectrum produced by integrating the Raman difference spectrum of B).
Figure 19:
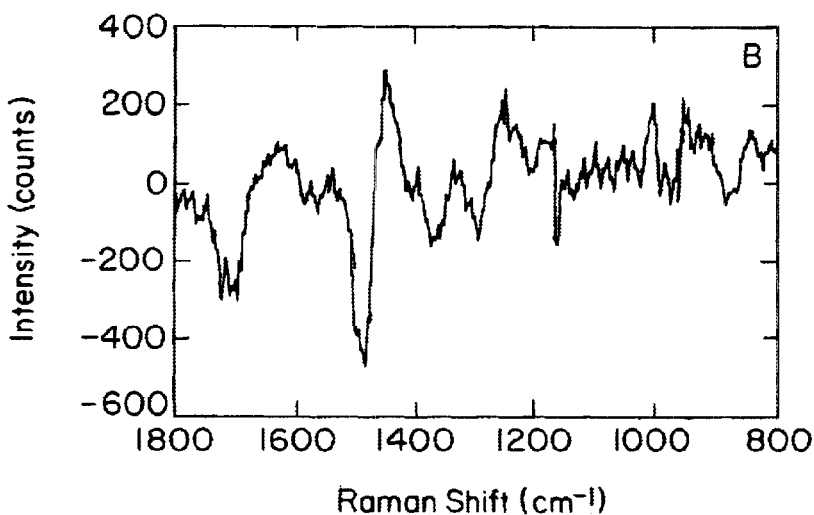
Figure 19:
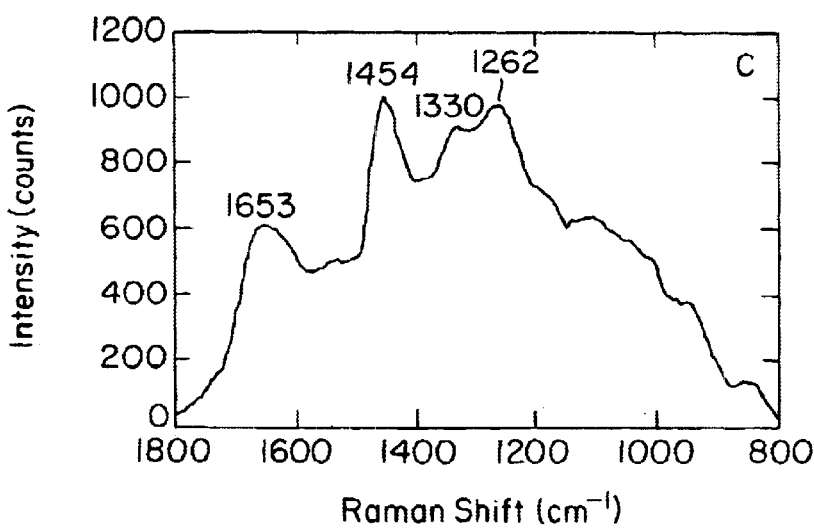

FIG. 19A shows the Raman spectra of a normal aorta sample excited with 810 nm laser light and collected with the spectrograph/CCD system 300. In this case, the broadband background emission, which is presumably due to tissue fluorescence, is roughly five times more intense than the strongest Raman bands at 1650, 1451, 1330, and 1253 cm$^{-1}$. In contrast, the 1064 nm FT-Raman study of normal human aorta shown in FIG. 2a exhibited Raman signals with the peak intensities of the strongest bands, amide I at 1650 cm$^{-1}$ and C—H bend at 1451 cm$^{-1}$, being roughly three times larger than the broadband background emission. However, this background emission in the spectrograph/CCD system is relatively weak with respect to the Raman signals (i.e., on the order of the Raman signals) and therefore the shot noise associated with detecting this background emission is substantially smaller than the Raman signals, allowing the Raman bands to be made distinct after the background emission signals are removed through filtering or subtraction. The shot noise is typically random noise exhibiting a Poisson distribution and is associated with the detector and/or the background emission itself.

In contrast, with visible excitations, the fluorescence background emission from the arterial pathology tissue types described is 3 to 4 orders of magnitude larger than the Raman signals, and the shot noise associated with this stronger background emission completely obscures the Raman bands even after the background emissions are removed. However, certain other types of tissue, e.g., colon and bladder, do not exhibit such high level fluorescence reactions at visible excitation frequencies, and therefore can probably operate with visible excitations.

The signal-to-noise ratio of the spectrum of normal aorta collected with the spectrograph/CCD system 300 with 20 mW incident power and 5 minutes collection time (FIG. 19A) is similar to that obtained with the FT-Raman system of FIG. 1C with 500 mW incident power and 35 minute collection time. Since the observed spectral signal-to-noise ratios are similar, we estimate that the noise level observed with the CCD detector 312 of FIG. 18 is roughly 3400 times less than that observed with the InGaAs detector 42 of FIG. 1C. For the InGaAs detector, the major noise source is the shot noise of the dark current, while with the CCD detector the dominant noise source is the shot noise of the broadband tissue emission, as the dark current and readout electrons of the CCD are much smaller than this emission.

This simple analysis has several important implications. First, since the major noise source encountered with the spectrograph/CCD system is shot noise from broadband emission by the tissue sample, the spectral signal-to-noise ratio is proportional to the square root of the product of incident intensity and the collection time.

The FT-Raman and spectrograph/CCD systems can be compared as follows. For the FT-Raman system, the incident intensity is 640 mW/mm$^2$. The quantum efficiency of the InGaAs detector at 1200 nm is 0.7, and the FT-spectrometer throughput is 1.1 mm$^2$sr, and the transmission efficiency of the FT-spectrometer and filters is roughly 0.062. For the spectrograph/CCD system, the incident intensity is 14 mW/mm$^2$. The CCD quantum efficiency is 0.15 at 900 nm, the spectrograph throughput is 0.043 mm$^2$sr, and the transmission efficiency of the spectrograph and filters is 0.24. Combining these factors and taking into account the $V^4$ dependence of the Raman cross-sections, the signal level measured by the FT-Raman spectrum is estimated to be 3400 times greater than that of the spectrograph/CCD spectrum.

Therefore, if the laser intensity is increased to the level employed in the FT-Raman experiments, the collection time could be reduced by a factor of 40, to 8 seconds, with no change in the spectral signal-to-noise ratio. Second, the noise level can be further reduced by using longer excitation wavelengths which minimize the tissue fluorescence emission. However, such reductions in fluorescence emission must be balanced against the decreasing quantum efficiency of the CCD at longer wavelengths, and the optimum excitation wavelength also depends on the fluorescence excitation profile of the tissue. For tissue types that exhibit little fluorescence emission at visible wavelengths, such as colon and bladder tissue, the CCD can be operated at visible or near visible wavelengths to take advantage of increased quantum efficiency of the CCD at these wavelengths. Finally, the throughput of a 500 µm core, 0.2 numerical aperture fused silica optical fiber is 0.03 mm²sr, which is roughly the same as that of the spectrograph/CCD system. This means that the present lens collection system can be replaced with an optical fiber probe, as is required for in vivo operation, with no additional loss in signal.

FIG. 19A shows that although the shot noise due to the broadband tissue emission is relatively small, the sloping broadband fluorescence emission still obscures the sharper Raman signals and complicates determination of peak frequencies and identification of weak bands. Furthermore, given the complexity of human tissue, it is likely that this broadband emission will be significant throughout the useful range of the CCD. Any quantitative analysis of the Raman bands in FIG. 19A requires that this broadband emission be first removed from the spectrum. The standard methods of removing fluorescence emission from Raman spectra utilize mathematical filters, which rely upon the fluorescence emission being relatively featureless. In an alternative method the excitation frequency is varied over a narrow range (10–30 cm$^{-1}$). The Raman band positions vary directly with the excitation frequency, while the fluorescence emission remains fairly constant with such small changes in excitation frequency, allowing it to be efficiently subtracted out. In contrast with mathematical filters, this operation requires no assumptions about the emission lineshape.

To implement this method, the Raman spectrum of the normal aorta specimen is recorded with excitation wavelengths of 810 nm (FIG. 19A) and 812 nm. The Raman bands shift with the excitation frequency by 30 cm$^{-1}$, while the fluorescence emission remains fairly constant. By subtracting these two spectra, the broadband emission is greatly reduced, and the Raman bands are more readily observed (FIG. 19B). This operation is mathematically analogous to taking the derivative of the Raman spectrum, so that the original Raman spectrum can be recovered by integrating the difference spectrum, as shown in FIG. 19C. The fluorescence background is greatly reduced in FIG. 19C as compared with FIG. 19A, allowing easier identification of the Raman bands and their peak frequencies. The integration also smooths the Raman spectrum over a bandwidth similar to the excitation frequency shift and causes some linewidth broadening, as is evident from FIG. 19C. Note that the accuracy of this method depends upon the high linearity and stability of the CCD array.

Figure 20A:
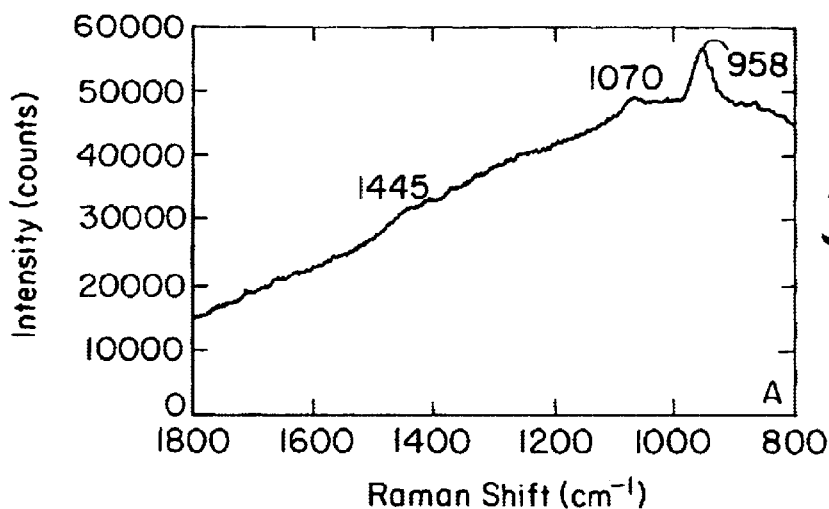
FIG. 20 graphically illustrates spectrograph/CCD-Raman spectra of an atherosclerotic plaque with a calcified deposit exposed at the surface: A) Raman plus fluorescence spectrum produced by illuminating the tissue sample with 810 nm laser light; B) Raman difference spectrum produced by subtracting spectra produced by illuminating the tissue sample with 810 and 812 nm laser light; C) resulting Raman spectrum produced by integrating the Raman difference spectrum of B).
Figure 20B:
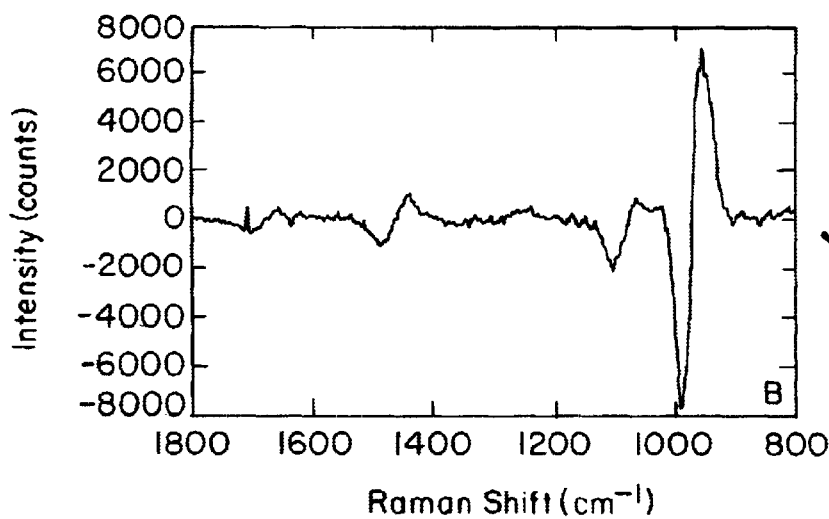
Figure 20C:
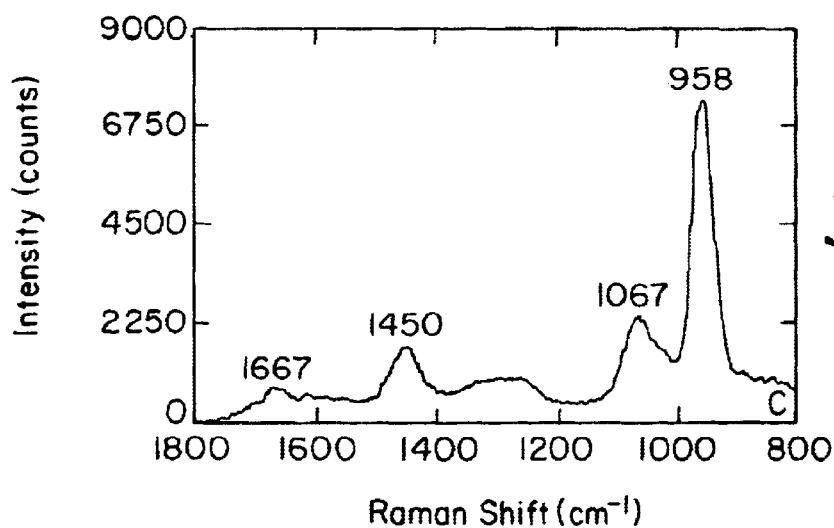

The NIR Raman spectrum of an atherosclerotic plaque with a calcified deposit exposed at the surface collected with the spectrograph/CCD system is shown in FIG. 20A. In this case, the broadband emission is nearly 10 times greater than that observed in normal aorta (FIG. 19A), resulting in increased noise. However, the intense phosphate stretching vibration at 960 cm$^{-1}$, due to the calcified salts, is readily identified. This band is sufficiently intense to be observed in real time and was used in aligning the collection optics. Some weaker bands may also be identified, such as the phosphate/carbonate band at 1070 cm$^{-1}$, although these are obscured by the large fluorescence background. By subtracting out this fluorescence (FIG. 20B), as above, these bands are much more easily distinguished. The Raman spectrum obtained by integrating the difference spectrum is shown in FIG. 20C. The broadband emission is reduced by a factor of 50 relative to Raman bands, and several weaker bands are readily observed. This spectrum is remarkably similar to that of FIG. 5a which was observed with the FT-Raman system and 1064 nm excitation.

Figure 21:
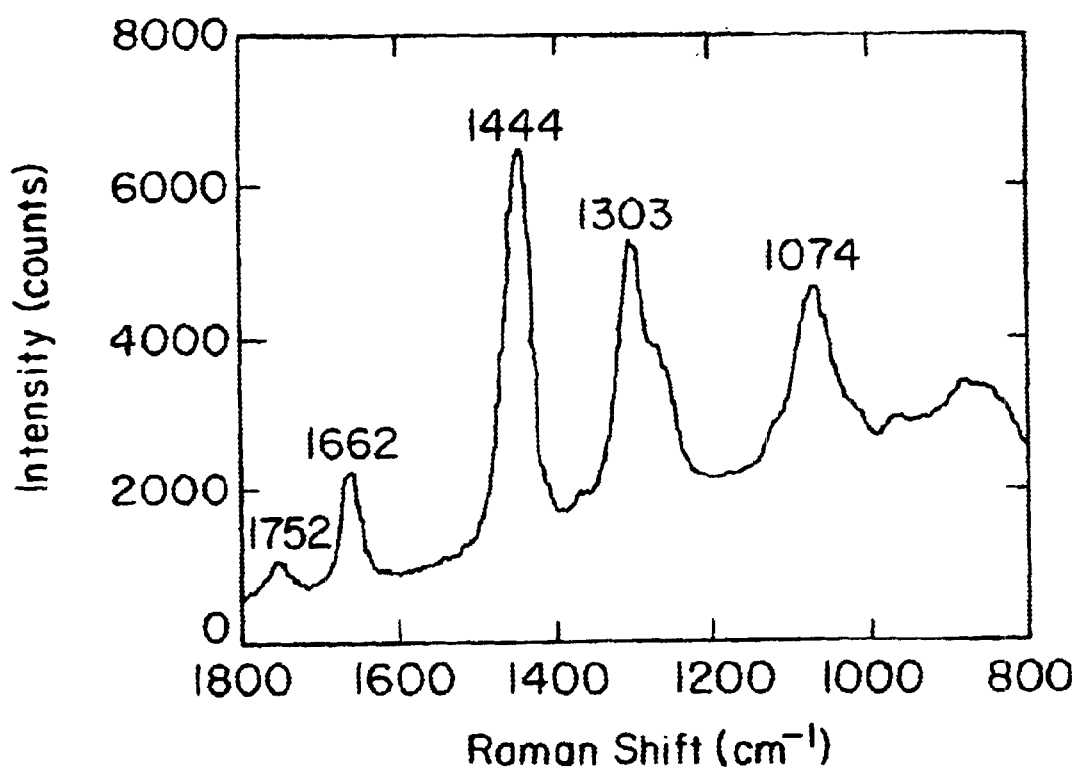
FIG. 21 graphically illustrates a spectrograph/CCD-Raman spectrum of adventitial adipose tissue.

As another example of the sensitivity of the spectrograph/CCD system 300, the Raman spectrum of adventitial adipose tissue is shown in FIG. 21, which can be compared to the FT-Raman spectrum shown in FIG. 5c. The broadband emission is similar to that of normal aorta, while the Raman bands, due mainly to triglycerides in the tissue, are very strong, resulting in an excellent spectral signal-to-noise ratio.

Thus, the spectrograph/CCD system with 810 nm excitation offers a faster alternative to FT-Raman with 1064 nm excitation and which has greater sensitivity. Even in complex mixtures such as human tissue, the level of background emission observed with 810 nm excitation is low enough to observe the Raman signals. This fluorescence emission does not excessively degrade the signal-to-noise ratio. By subtracting two spectra collected at slightly different excitation wavelengths, and then integrating the difference spectrum, this broadband emission is rejected, yielding high quality Raman spectra. Deconvolution techniques can also be used to selectively remove, or reduce, Raman, fluorescence, or noise light components. Improvements such as using a CW laser to increase the incident intensity and a back-thinned CCD having better red response allows Raman spectra to be collected from intact human tissue in under 1 second. Longer excitation wavelengths may reduce the background emission further. Implementation of the spectrograph/CCD system with a high power diode laser and an optical fiber probe will provide a compact, mobile system for rapidly acquiring NIR Raman spectra remotely from human tissues and will provide a powerful tool for in vivo clinical applications.

Equivalents

Those skilled in the art will recognize, or be able to ascertain using routine experimentation, many equivalents to the specific embodiments of the invention described herein. These and all other equivalents are intended to be encompassed by the following claims.

What is claimed is:

1. A method of spectroscopic diagnosis of tissue of a patient comprising:

irradiating a portion of the tissue of a patient to be diagnosed with laser radiation directed onto the tissue through a fiber optic cable with a first frequency and then irradiating the same portion of tissue with a second frequency slightly shifted from the first frequency;

detecting light emitted by the portion of tissue in response to irradiation by the first frequency to generate a first spectrum of emitted light frequency components, detecting light emitted by the tissue in response to irradiation by the second frequency to generate a second spectrum of emitted light frequency components, and generating a difference spectrum from the first spectrum and the second spectrum by subtracting one from the other, the difference spectrum containing substantially the Raman shifted frequency components of the first spectrum and the second spectrum and detecting light emitted by the tissue with a charge coupled device that is optically coupled to a proximal end of the fiber optic cable, the device collecting the light for a period of 5 minutes or less, the light having a Raman shifted frequency component different from the first and second irradiating frequencies and further having background light components having shot noise levels below the level of the Raman light component;

removing the background light components from the detected light to leave substantially the Raman shifted frequency light components; and analyzing the remaining detected light to diagnose a condition of the portion of tissue.

2. The method of claim 1 wherein the first and second irradiation frequencies have wavelengths of between 750 nm and 900 nm, and the second frequency is shifted from the first frequency by less than 50 cm$^{-1}$.

3. The method of claim 1 wherein the detecting step further comprises generating the first spectrum and the second spectrum of the emitted light frequency components with a spectrometer and detecting the first spectrum and the second spectrum with the charge coupled device.

4. The method of claim 3 further including the steps of providing a spectrometer comprising a single stage spectroscope.

5. The method of claim 3 further comprising electronically generating the difference spectrum with a computer from the first and second spectra detected with the charge coupled device.

6. The method of spectroscopic diagnosis of claim 1 wherein the detecting step further comprises generating a spectrum of the emitted light frequency components with a spectrometer and detecting the spectrum with the charge coupled device.

7. The method of spectroscopic diagnosis of claim 6 wherein the fiber optic cable receives light emitted by the tissue and transmits the emitted light to the spectrometer.

8. The method of spectroscopic diagnosis of claim 7 further comprising providing a single stage spectrometer.

9. The method of spectroscopic diagnosis of claim 6 further comprising an optical needle to which the radiation is coupled for delivery to the tissue.

10. The method of spectroscopic diagnosis of claim 6 further comprising detecting light reflected by the tissue and analyzing the reflected light to diagnosis the tissue.

11. The method of spectroscopic diagnosis of claim 1 further comprising providing a catheter, through which the fiber optic cable extends, for insertion into body lumens.

12. A method of spectroscopic diagnosis of tissue comprising:

irradiating a portion of tissue of a patient to be diagnosed with laser radiation having at least first and second irradiating frequencies in the infrared range that are directed through a fiber optic cable;

detecting light emitted by the portion of tissue in response to the laser radiation with a charge coupled device that is optically coupled to a proximal end of the fiber optic cable, the device collecting light from the portion of tissue for a period of 5 minutes or less, the detected light having a Raman shifted frequency component different from the first and second irradiating frequencies, removing background components from the detected light to provide corrected Raman spectral data; and analyzing the corrected Raman spectral data to diagnose a condition of the portion of the tissue.

13. The method of claim 12 further comprising collecting light emitted by the tissue for a period of eight seconds or less.

14. The method of claim 12 further comprising collecting light emitted by the tissue for a period of one second or less.

15. The method of claim 12 further comprising altering the frequency of the infrared radiation to alter a depth of penetration of the radiation into tissue.

16. The method of claim 12 further comprising altering an angle of incidence of the radiation relative to the portion of tissue to alter a depth of penetration of the radiation into the portion of tissue.

* * * * *